(12) United States Patent
Blaauw et al.

(10) Patent No.: US 9,388,156 B2
(45) Date of Patent: Jul. 12, 2016

(54) CHROMANYL DERIVATIVES FOR TREATING MITOCHONDRIAL DISEASE

(71) Applicant: Khondrion IP B.V., Beuningen Gld (NL)

(72) Inventors: Richard Hendrik Blaauw, Nijmegen (NL); Ruben Gerardus George Leenders, Nijmegen (NL); Geert Jan Sterk, Utrecht (NL); Pedro Harold Han Hermkens, Oss (NL)

(73) Assignee: Khondiron IP B.V., Beuningen (NL)

( * ) Notice: Subject to any disclaimer, the term of this patent is extended or adjusted under 35 U.S.C. 154(b) by 0 days.

(21) Appl. No.: 14/414,055

(22) PCT Filed: Jul. 12, 2013

(86) PCT No.: PCT/NL2013/050528
§ 371 (c)(1),
(2) Date: Jan. 9, 2015

(87) PCT Pub. No.: WO2014/011047
PCT Pub. Date: Jan. 16, 2014

(65) Prior Publication Data
US 2015/0166501 A1 Jun. 18, 2015

Related U.S. Application Data

(60) Provisional application No. 61/670,644, filed on Jul. 12, 2012.

(30) Foreign Application Priority Data

Jul. 12, 2012 (EP) .................................. 12176128

(51) Int. Cl.
*C07D 311/66* (2006.01)
*A61Q 19/08* (2006.01)
*C07D 413/12* (2006.01)
*A61K 8/49* (2006.01)

(52) U.S. Cl.
CPC .............. *C07D 311/66* (2013.01); *A61K 8/498* (2013.01); *A61Q 19/08* (2013.01); *C07D 413/12* (2013.01); *A61K 2800/74* (2013.01)

(58) Field of Classification Search
CPC .... C07D 311/66; C07D 413/12; A61K 8/498; A61K 2800/74; A61Q 19/08
See application file for complete search history.

(56) References Cited

U.S. PATENT DOCUMENTS 6,727,239 B1 4/2004 Chabrier De Lassauniere et al.
2009/0118257 A1 5/2009 Jankowski et al.

FOREIGN PATENT DOCUMENTS

JP 2002-047272 A 2/2002
WO WO-01/81324 A1 11/2001

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Distelmaier, F. et al., "Trolox-Sensitive Reactive Oxygen Species Regulate Mitochondrial Morphology, Oxidative Phosphorylation and Cytosolic Calcium Handling in Healthy Cells", Antioxidants & Redox Signaling, Jun. 13, 2012.
International Search Report of PCT/NL2013/050528 mailed Oct. 8, 2013.
Proni, G. et al., "Magnesium Tetraarylporphyrin Tweezer: A CD-Sensitive Host for Absolute Configurational Assignments of [alpha]-Chiral Carboxylic Acids", Journal of the American Chemical Society, vol. 125, No. 42, Oct. 1, 2003, pp. 12914-12927.

* cited by examiner

*Primary Examiner* — Kristin Vajda
(74) *Attorney, Agent, or Firm* — Foley & Lardner LLP; Sunit Talapatra

(57) ABSTRACT

The invention relates to novel compounds that are useful for modulating mitochondrial morphology and/or expression of OXPHOS enzymes and/or cellular ROS. The compounds are derivatives of TroloxrM wherein the carboxylic acid moiety is replaced by an amide moiety and wherein the nitrogen atom of the amide moiety is connected via a linker to a cationic nitrogen atom. The compounds of the invention are formulated into pharmaceutical or cosmetic compositions. The invention further relates to methods wherein the compounds of the invention are used for treating or preventing mitochondrial disorders, conditions associated with mitochondrial dysfunction, including adverse drug effects, and/or neoplastic diseases. The invention also relates to cosmetic methods for treating or delaying further aging of the skin and veterinary applications.

(I)

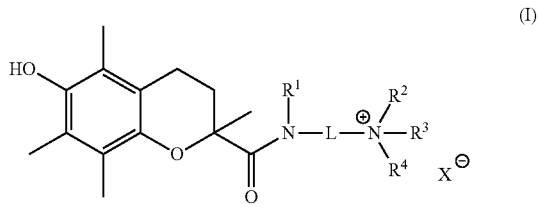

17 Claims, 5 Drawing Sheets

CHROMANYL DERIVATIVES FOR TREATING MITOCHONDRIAL DISEASE

CROSS-REFERENCE TO RELATED APPLICATIONS

This application is the National Phase of International Patent Application No. PCT/NL2013/050528, filed Jul. 12, 2013, published as WO 2014/011047, which claims priority to European Application No. 12176128.2 and U.S. Provisional Application No. 61/670,644, both filed Jul. 12, 2012. The contents of these applications are herein incorporated by reference in their entirety.

FIELD OF THE INVENTION

The invention relates to the field human and animal disease and cosmetics. The invention in particular relates to compounds such as Trolox™-derivatives for treating conditions that are associated with mitochondrial dysfunction or mitochondrial deficiencies, including adverse drug effects causing mitochondrial dysfunction, for treating neoplastic diseases and for cosmetic use against aging of the skin.

BACKGROUND OF THE INVENTION

Mitochondria are essential organelles that constitute the 'powerhouses' of the cell. Defects in these organelles often lead to a variety of severe metabolic disorders affecting the organs that have a high-energy demand, such as muscle and brain. With an incidence of at least 1 in 5000 individuals it is recognized as the most common group of inborn errors of metabolism. Moreover, because programmed cell death (apoptosis) is triggered by mitochondria, defects in these organelles have consequences far beyond the diseases, which brought them initially to our attention and involvement in cancer and neurodegenerative diseases like Alzheimer and Parkinson has been demonstrated. Many commonly used drugs like the NRTIs, certain antibiotics and anti-epileptic drugs, may cause mitochondrial dysfunction. So far no effective treatment is available to cure or improve these disease conditions.

One of the primary functions of mitochondria is oxidative phosphorylation (OXPHOS). The molecule adenosine triphosphate (ATP) functions as an energy "currency" or energy carrier in the cell, and eukaryotic cells derive the majority of their ATP from biochemical processes carried out by mitochondria, including the citric acid cycle, which generates reduced $NADH+H^+$ from oxidized $NAD^+$, and OXPHOS, during which $NADH+H^+$ is oxidized back to $NAD^+$. The electrons released by oxidation of $NADH+H^+$ are shuttled down a series of protein complexes (Complex I, Complex II, Complex III, and Complex IV) known as the mitochondrial respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

The contribution of mitochondrial dysfunction to human disease was already recognised in the late 1980s, when maternally inherited point mutations, as well as deletions arising spontaneously during development, were found to be associated with rare neurological syndromes. Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. Some examples of mitochondrial diseases are Friedreich's ataxia (FRDA), Leber's Hereditary Optic Neuropathy (LHON), dominant optic atrophy (DOA); mitochondrial myopathy, encephalopathy, lactacidosis, and stroke (MELAS), Myoclonus Epilepsy Associated with Ragged-Red Fibers (MERRF) syndrome, Leigh syndrome, and oxidative phosphorylation disorders. Most mitochondrial diseases involve children who manifest the signs and symptoms of accelerated aging, including neurodegenerative diseases, stroke, blindness, hearing impairment, diabetes, and heart failure.

Very few treatments are available for patients suffering from these mitochondrial diseases. The drug idebenone (a $CoQ_{10}$ variant) has been approved for the treatment of Friedreich's ataxia (Bent et al., 2010, Trends Mol Med, 16:210-7; Klopstock et al., 2011, Brain, 134:2677-86). Another compound, $MitoQ_{10}$ (mitoquinone), has been proposed for treating mitochondrial disorders (U.S. Pat. No. 7,179,928) but clinical results for MitoQ have not yet been reported. A successful treatment strategy has been developed for patients with a secondary mitochondrial disorder involving Ullrich's congenital muscular dystrophy and Bethlem's myopathy. The pathogenic mechanism in these myopathies involves inappropriate opening of the mitochondrial permeability transition pore. This action was prevented in patients treated with the permeability-transition-pore desensitizer CSA (cyclosporin A; Angelin et al., 2007, Proc Natl Acad Sci USA, 104:991-6; Merlini et al., 2008, Proc Natl Acad Sci USA, 105:5225-9).

An overview of current clinical trials relating to mitochondrial disease can be found online (www.clinicaltrials.gov/c2/results?term=mitochondrial+disease); these include studies of CoQ10 for the treatment of muscle weakness and mitochondrial diseases, dietary supplements for MELAS, EPI-743 for mitochondrial diseases, human growth hormone for obesity, nutritional therapy for diabetes, pioglitazone for diabetes, idebenone for MELAS, and vitamin E for mitochondrial trifunctional protein deficiency.

WO 2012/019032 discloses methods of treatment, prevention, or suppression of symptoms associated with a mitochondrial disorder and/or modulating, normalizing, or enhancing one or more energy biomarkers one or more energy, whereby vitamin K analogues are administered.

WO 2012/019029 discloses methods of treatment, prevention, or suppression of symptoms associated with a mitochondrial disorder and/or modulating, normalizing, or enhancing one or more energy biomarkers one or more energy, whereby naphtoquinones and derivatives thereof are administered.

Distelmaier et al. (Antioxid Redox Signal. 2012, Jun. 13 (in press), PMID 22559215) disclose that Trolox™ (6-hydroxy-2,5,7,8-tetramethylchroman-2-carboxylic acid) reduces the levels of ROS, increased mitofusins-mediated mitochondrial filamentation and expression of mitochondrial complex I, activity of citrate synthase and OXPHOS enzymes and cellular $O_2$ consumption in cultured healthy human skin fibroblasts.

There is however still a need in the art for effective means for modulating mitochondrial function for them to be used in treatments of mitochondrial disease and/or conditions associated with mitochondrial dysfunction, in the treatment of neoplastic disease or for cosmetic use.

SUMMARY OF THE INVENTION

In a first aspect the invention relates to a compound of general formula (I):

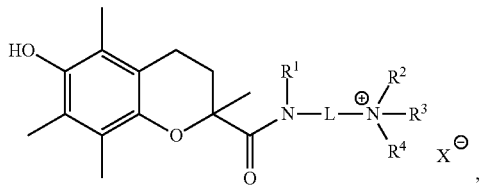

wherein
L is a linker comprising 1 to 10 optionally substituted backbone atoms selected from carbon, nitrogen and oxygen; and
$R^1$ and $R^2$ are each independently selected from hydrogen and $C_1$-$C_6$ alkyl, or $R^1$ and $R^2$ are joined together to form a second linker between the amide nitrogen atom and the cationic nitrogen atom, or $R^1$ is joined with a backbone atom of the linker L in a cyclic structure and/or $R^2$ is joined with a backbone atom of the linker L in a cyclic structure; and
$R^3$ is selected from hydrogen and $C_1$-$C_6$ alkyl, wherein the alkyl moiety may be substituted with one or more halogen atoms or (halo)alkoxy moieties, or $R^3$ is absent when the cationic nitrogen atom is part of an imine moiety; and
$R^4$ is selected from hydrogen and $C_1$-$C_6$ alkyl, wherein the alkyl moiety may be substituted with one or more halogen atoms or (halo)alkoxy moieties; and
$X^-$ is a pharmaceutically acceptable anion.

Preferably the compound according to the invention is a compound wherein:
L=$L^1$, $R^1$=$R^2$=$L^1$, $R^3$=H, $R^4$=H, X=Cl; or
L=$L^1$, $R^1$=H, $R^2$=H, $R^3$=H, $R^4$=H; X=Cl; or
L=$L^2$, $R^1$=H, $R^2$=H, $R^3$=H, $R^4$=H; X=Cl; or
L=$L^3$, $R^1$=H, $R^2$=H, $R^3$=H, $R^4$=H; X=Cl; or
L=$L^4$, $R^1$=H, $R^2$=H, $R^3$=absent, $R^4$=H; X=TFA; or
L=$L^5$, $R^1$=H, $R^2$=H, $R^3$=absent, $R^4$=H; X=TFA; or
L=$L^6$, $R^1$=H, $R^2$=H, $R^3$=absent, $R^4$=H; X=TFA; or
L=$L^3$, $R^1$=H, $R^2$=Me, $R^3$=Me, $R^4$=Me; X=I; or
L=$L^1$, $R^1$=H, $R^2$=Me, $R^3$=Me, $R^4$=Me; X=I; or
L=$L^7$, $R^1$=H, $R^2$=H, $R^3$=absent, $R^4$=H; X=Cl; or
L=$L^8$, $R^1$=H, $R^2$=H, $R^3$=absent, $R^4$=H; X=Cl; or
L=$L^9$, $R^1$=H, $R^2$=H, $R^3$=absent, $R^4$=H; X=Cl; or
L=$L^{10}$, $R^1$=$R^{1'}$=$L^1$, $R^2$=H, $R^3$=bsent, $R^4$=H; X=TFA; or
L=$L^{11}$, $R^1$=H, $R^2$=H, $R^3$=H, $R^4$=H; X=Cl; or
L=$L^1$, $R^1$=H, $R^2$=H, $R^3$=absent, $R^4$=H; X=Cl; or
L=$L^{13}$, $R^1$=H, $R^2$=H, $R^3$=H, $R^4$=H; X=Cl; or
L=$L^{14}$, $R^1$=H, $R^2$=H, $R^3$=H, $R^4$=H; X=Cl; or
L=$L^{15}$, $R^1$=H, $R^2$=H, $R^3$=H, $R^4$=H; X=Cl; or
L=$L^{11}$, $R^1$=H, $R^2$=Me, $R^3$=Me, $R^4$=H; X=Cl; or
L=$L^{16}$, $R^1$=H, $R^2$=H, $R^3$=H, $R^4$=H; X=Cl; or
L=$L^{17}$, $R^1$=H, $R^2$=H, $R^3$=H, $R^4$=H; X=Cl; or
L=$L^{16}$, $R^1$=H, $R^2$=Me, $R^3$=Me, $R^4$=H; X=Cl; or
L=$L^{18}$, $R^1$=H, $R^2$=$R^{2'}$=$L^3$, $R^3$=H, $R^4$=H; X=Cl; or
L=$L^{19}$, $R^1$=H, $R^2$=$R^{2'}$=$L^3$, $R^3$=H, $R^4$=H; X=Cl; or
L=$L^{20}$, $R^1$=H, $R^2$=H, $R^6R^{6'}$=$L^3$, $R^3$=absent, $R^4$=H; X=Cl; or
L=$L^{21}$, $R^1$=H, $R^2$=$R^{2'}$=$L^1$, $R^3$=H, $R^4$=H; X=Cl; or
L=$L^{22}$, $R^1$=$R^{1'}$=$L^1$, $R^2$=H, $R^3$=H, $R^4$=H; X=Cl; or
L=$L^{23}$, $R^1$=$R^{1'}$=$L^1$, $R^2$=H, $R^3$=H, $R^4$=H; X=Cl; or
L=$L^{24}$, $R^1$=$R^{1'}$=$L^3$, $R^2$=H, $R^3$=H, $R^4$=H; X=Cl; or
L=$L^{25}$, $R^1$=$R^{1'}$=$L^3$, $R^2$=H, $R^3$=absent, $R^4$=H; X=Cl; or
L=$L^{26}$, $R^1$=H, $R^2$=H, $R^6R^{6'}$=$L^1$, $R^3$=H, $R^4$=H; X=Cl; or
L=$L^{19}$, $R^1$=H, $R^2R^{2'}$=$L^3$, $R^3$=Me, $R^4$=H; X=Cl; or
L=$L^{19}$, $R^1$=H, $R^2R^{2'}$=$L^1$, $R^3$=H, $R^4$=H; X=Cl; or
L=$L^{21}$, $R^1$=H, $R^2R^{2'}$=$L^1$, $R^3$=Me, $R^4$=H; X=Cl.

In a one preferred embodiment, the compound according to the invention is a compound wherein:
L=$L^5$, $R^1$=H, $R^2$=H, $R^3$=absent, $R^4$=H; X=TFA; or
L=$L^8$, $R^1$=H, $R^2$=H, $R^3$=absent, $R^4$=H; X=Cl; or
L=$L^{11}$ $R^1$=H, $R^2$=H, $R^3$=H, $R^4$=H; X=Cl; or
L=$L^1$, $R^1$=H, $R^2$=H, $R^3$=absent, $R^4$=H; X=Cl; or
L=$L^{17}$, $R^1$=H, $R^2$=H, $R^3$=H, $R^4$=H; X=Cl; or
L=$L^{16}$, $R^1$=H, $R^2$=Me, $R^3$=Me, $R^4$=H; X=Cl; or
L=$L^{19}$, $R^1$=H, $R^2$=$R^{2'}$=$L^3$, $R^3$=H, $R^4$=H; X=Cl; or
L=$L^{21}$, $R^1$=H, $R^2$=$R^{2'}$=$L^1$, $R^3$=H, $R^4$=H; X=Cl; or
L=$L^{26}$, $R^1$=H, $R^2$=H, $R^5R^{5'}$=$L^1$, $R^3$=H, $R^4$=H; X=Cl; or
L=$L^{19}$, $R^1$=H, $R^2$=$R^{2'}$=$L^3$, $R^3$=Me, $R^4$=H; X=Cl; or
L=$L^{21}$, $R^1$=H, $R^2$=$R^{2'}$=$L^1$, $R^3$=Me, $R^4$=H; X=Cl.

In another preferred embodiment, the compound according to the invention is a compound wherein:
L=$L^3$, $R^1$=H, $R^2$=Me, $R^3$=Me, $R^4$=Me; X=I; or
L=$L^1$, $R^1$=H, $R^2$=Me, $R^3$=Me, $R^4$=Me; X=I.

In a second aspect, the invention pertains to a pharmaceutical or cosmetic composition comprising a compound according to the invention.

In a third aspect, the invention pertains to a compound according to the invention, for use as a medicament.

In a fourth aspect, the invention pertains to a compound according to the invention, for use in modulating at least one of mitochondrial morphology and expression of OXPHOS enzymes.

In a fifth aspect, the invention pertains to a compound according to the invention, for use in treating, preventing, or suppressing symptoms associated with a mitochondrial disorder or with a condition associated with mitochondrial dysfunction, wherein, preferably the compound is a compound wherein:
L=$L^5$, $R^1$=H, $R^2$=H, $R^3$=absent, $R^4$=H; X=TFA; or
L=$L^8$, $R^1$=H, $R^2$=H, $R^3$=absent, $R^4$=H; X=Cl; or
L=$L^{11}$, $R^1$=H, $R^2$=H, $R^3$=H, $R^4$=H; X=Cl; or
L=$L^1$, $R^1$=H, $R^2$=H, $R^3$=absent, $R^4$=H; X=Cl; or
L=$L^{17}$, $R^1$=H, $R^2$=H, $R^3$=H, $R^4$=H; X=Cl; or
L=$L^{16}$, $R^1$=H, $R^2$=Me, $R^3$=Me, $R^4$=H; X=Cl; or
L=$L^{19}$, $R^1$=H, $R^2R^{2'}$=$L^3$, $R^3$=H, $R^4$=H; X=Cl; or
L=$L^{21}$, $R^1$=H, $R^2R^{2'}$=$L^1$, $R^3$=H, $R^4$=H; X=Cl; or
L=$L^{26}$, $R^1$=H, $R^2$=H, $R^5R^{5'}$=$L^1$, $R^3$=H, $R^4$=H; X=Cl; or
L=$L^{19}$, $R^1$=H, $R^2R^{2'}$=$L^3$, $R^3$=Me, $R^4$=H; X=Cl; or
L=$L^{21}$, $R^1$=H, $R^2R^{2'}$=$L^1$, $R^3$=Me, $R^4$=H; X=Cl.

Preferably in the fifth aspect, the mitochondrial disorder is a disorder selected from the group consisting of: Myoclonic epilepsy; Myoclonic Epilepsy with Ragged Red Fibers (MERRF); Leber's Hereditary Optic Neuropathy (LHON); neuropathy ataxia and retinitis pigmentosa (NARP); Mitochondrial Myopathy, Encephalopathy, Lactacidosis, Stroke (MELAS); Leigh syndrome; Leigh-like syndrome; Dominant Optic atrophy (DOA); Kearns-Sayre Syndrome (KSS); Maternally Inherited Diabetes and Deafness (MIDD); Alpers-Huttenlocher syndrome; Ataxia Neuropathy spectrum; Chronic Progressive External Ophthalmoplegia (CPEO);

Pearson syndrome; Mitochondrial Neuro-Gastro-Intestinal Encephalopathy (MNGIE); Sengers syndrome; 3-methylglutaconic aciduria, sensorineural deafness, encephalopathy and neuro-radiological findings of Leigh-like syndrome (MEGDEL); myopathy; mitochondrial myopathy; cardiomyopathy; and encephalomyopathy, SURF1 (COX deficient Leigh syndrome due to complex IV surfeit protein deficiency) and isolated or combined OXPHOS deficiencies with so far unsolved genetic defect including disturbed pyruvate oxidation and ATP plus PCr production rates.

Preferably in the fifth aspect, the condition associated with mitochondrial dysfunction is a condition selected from the group consisting of: Friedreich's Ataxia (FRDA); renal tubular acidosis; retinopathy, Parkinson's disease; Alzheimer's disease; amyotrophic lateral sclerosis (ALS); Huntington's disease; developmental pervasive disorders; hearing loss; deafness; diabetes; ageing and adverse drug effects leading to mitochondrial dysfunction.

Further preferred in the fifth aspect, a measurable clinical marker is used to assess the efficacy of the therapy using the compounds if the invention, whereby, preferably, the clinical marker is one or more markers selected from the group consisting of lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; amino acids, in particular alanine, citrulline and proline in whole blood, plasma or cerebrospinal fluid, organic acids in body fluids; FGF21 in serum and skeletal muscle; phosphocreatine levels, NADH (NADH+H$^+$) or NADPH (NADPH+H$^+$) levels; NAD or NADP levels; ATP levels; anaerobic threshold; reduced coenzyme Q (CoQ$^{red}$) levels; oxidized coenzyme Q (CoQ$^{ox}$ levels; total coenzyme Q (CoQ$^{tot}$) levels; oxidized cytochrome C levels; reduced cytochrome C levels; oxidized cytochrome C/reduced cytochrome C ratio; acetoacetate levels, beta-hydroxy butyrate levels, acetoacetate/betahydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2).

In a sixth aspect, the invention pertains to a compound according to the invention, for use in treating, preventing, or suppressing symptoms associated with a neoplastic disease, wherein, preferably the compound is a compound wherein:
L=L$^3$, R$^1$=H, R$^2$=Me, R$^3$=Me, R$^4$=Me; X=I; or
L=L$^1$, R$^1$=H, R$^2$=Me, R$^3$=Me, R$^4$=Me, X=I.

Preferably in the sixth aspect, the neoplastic disease is cancer, preferably a cancer selected from the group comprising basal cell carcinoma, bone cancer, bowel cancer, brain cancer, breast cancer, cervical cancer, leukemia, liver cancer, lung cancer, lymphoma, melanoma, ovarian cancer, pancreatic cancer, prostate cancer or thyroid cancer.

In a seventh aspect, the invention relates to a cosmetic method for treating or delaying further aging of the skin in a subject, the method comprising the step of administering to the skin of the subject an effective amount of a composition comprising a compound according to the invention, wherein preferably the compound is a compound wherein:
L=L$^5$, R$^1$=H, R$^2$=H, R$^3$=absent, R$^4$=H; X=TFA; or
L=L$^8$, R$^1$=H, R$^2$=H, R$^3$=absent, R$^4$=H; X=Cl; or
L=L$^{11}$, R$^1$=H, R$^2$=H, R$^3$=H, R$^4$=H; X=Cl; or
L=L$^1$, R$^1$=H, R$^2$=H, R$^3$=absent, R$^4$=H; X=Cl; or
L=L$^{17}$, R$^1$=H, R$^2$=H, R$^3$=H, R$^4$=H; X=Cl; or
L=L$^{16}$, R$^1$=H, R$^2$=Me, R$^3$=Me, R$^4$=H; X=Cl; or
L=L$^{19}$, R$^1$=H, R$^2$=R$^{2'}$=L$^3$, R$^3$=H, R$^4$=H; X=Cl; or
L=L$^{21}$, R$^1$=H, R$^2$=R$^{2'}$=L$^1$, R$^3$=H, R$^4$=H; X=Cl; or
L=L$^{26}$, R$^1$=H, R$^2$=H, R$^5$R$^{5'}$=L$^1$, R$^3$=H, R$^4$=H; X=Cl; or
L=L$^{19}$, R$^1$=H, R$^2$R$^{2'}$=L$^3$, R$^3$=Me, R$^4$=H; X=Cl; or
L=L$^{21}$, R$^1$=H, R$^2$R$^{2'}$=L$^1$, R$^3$=Me, R$^4$=H; X=Cl.

In an eighth aspect, the invention relates to a method of treating, preventing, or suppressing symptoms associated with a mitochondrial disorder or with a condition associated with mitochondrial dysfunction, the method comprising administering to a subject an effective amount of compound according to the invention. In the method the mitochondrial disorder preferably is a disorder as herein defined above or the condition preferably is a condition as herein defined above. Further preferred in the method, a measurable clinical marker is used to assess the efficacy of the therapy using the compounds if the invention, whereby preferably, the clinical marker is one or more markers selected from the group consisting of lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+H$^+$) or NADPH (NADPH+H$^+$) levels; NAD or NADP levels; ATP levels; anaerobic threshold; reduced coenzyme Q (Coe) levels; oxidized coenzyme Q (CoQ$^{ox}$ levels; total coenzyme Q (CoQ$^{tot}$) levels; oxidized cytochrome C levels; reduced cytochrome C levels; oxidized cytochrome C/reduced cytochrome C ratio; acetoacetate levels, beta-hydroxy butyrate levels, acetoacetate/betahydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2).

DESCRIPTION OF THE INVENTION

In a first aspect the invention pertains to a compound which is a derivative of 6-hydroxy-2,5,7,8-tetramethyl chroman-2-carboxylic acid, which is also known under its trade name Trolox™. In a compound of the invention, the carboxylic acid moiety is replaced by an amide moiety, wherein the nitrogen atom of the amide moiety is connected via a linker to a cationic nitrogen atom. This cationic nitrogen atom preferably formally originates from protonation or alkylation, preferably protonation or methylation of a trivalent nitrogen atom. The trivalent nitrogen atom is preferably an amine moiety, either primary, secondary or tertiary, or an imine moiety, either primary or secondary. The counter ion (X$^-$) of the cationic nitrogen atom is a negatively charged ion, preferably a monovalent negatively charged ion, more preferably an anion as indicated herein below.

The synthesis of the compounds of the invention does not need to encompass the protonation or alkylation of an amine or imine nitrogen atom. The cationic nitrogen atom may also be formed via a different route. As such, the cationic nitrogen atom only "formally" originates from the protonation or alkylation of an amine or imine nitrogen atom.

The compound of the invention may be identified by general formula (I):

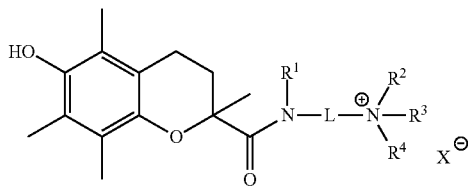

Herein,
L is a linker between the amide nitrogen atom and the cationic nitrogen atom; and
$R^1$ and $R^2$ are each independently selected from hydrogen (H) or $C_1$-$C_6$ alkyl, or $R^1$ and $R^2$ are joined together and thus form a second linker between the amide nitrogen atom and the cationic nitrogen atom, or $R^1$ is joined with a backbone atom of the linker L in a cyclic structure and/or $R^2$ is joined with a backbone atom of the linker L in a cyclic structure; and
$R^3$ is selected from hydrogen (H) or $C_1$-$C_6$ alkyl, wherein the alkyl moiety may be substituted with one or more halogen atoms or (halo)alkoxy moieties, or $R^3$ is absent when the cationic nitrogen atom is part of an imine moiety; and
$R^4$ is selected from hydrogen (H) or $C_1$-$C_6$ alkyl, wherein the alkyl moiety may be substituted with one or more halogen atoms or (halo)alkoxy moieties; and
$X^-$ is an anion, preferably a pharmaceutically acceptable anion.

The compound identified by general formula (I) comprises at least one chiral carbon atom (stereocenter), i.e. the atom at the 2-position of the Trolox™-moiety. Both the compound having an S-configuration as the compound having an R-configuration of the carbon atom at the 2-position are encompassed in the present invention, as well as mixtures of the different stereoisomers. Such a mixture may have one of the configurations in enantiomeric excess, or may be racemic. Whenever an additional stereocenter is present in the compound according to the invention, for example in the linker, it may exists as the S-configuration, as the R-configuration, or as a mixture of both configurations. Such a mixture may have one of the configurations in enantiomeric excess, or may be racemic. If more than one stereocenter is present in the compound according to the invention, the above holds true for each stereocenter independently.

When the cationic nitrogen atom is part of an imine moiety, the linker L comprises at least one double bond, located between the cationic nitrogen atom and the adjacent backbone atom of the linker. In such an instance, $R^3$ is absent. When the cationic nitrogen atom is part of an amine moiety, it is connected to the linker via a single bond, and $R^3$ is present. In the instance that $R^3$ is present, $R^3$ is selected from hydrogen (H) or $C_1$-$C_6$ alkyl, wherein the alkyl moiety may be substituted with one or more halogen atoms or (halo) alkoxy moieties, preferably $R^3$ is H or $C_1$-$C_4$ alkyl, wherein the alkyl moiety may be substituted with one or more halogen atoms or (halo)alkoxy moieties, more preferably $R^3$ is H or $C_1$-$C_2$ alkyl, wherein the alkyl moiety may be substituted with one or more halogen atoms or (halo)alkoxy moieties. Halogen atoms include fluorine (F), chlorine (Cl), bromine (Br), iodine (I), and astatine (At), preferably the halogen atom is fluorine (F). Preferred alkoxy moieties include methoxy and ethoxy. In haloalkoxy moieties, at least one hydrogen atom of an alkoxy moiety is replaced by a halogen atom, preferably by F. Suitable moieties for $R^3$ include, preferably are limited to, H, methyl (Me), trifluoromethyl ($CF_3$), ethyl (Et), isopropyl (iPr), cyclopropyl (-cPr), methylene cyclopropyl (—$CH_2$cPr), n-propyl (n-Pr), 2,2,2-trifluoroethyl (—$CH_2CF_3$), methoxymethyl (—$CH_2OCH_3$). More preferably $R^3$ is H or methyl (Me), most preferably $R^3$ is H. Alternatively, $R^3$ is preferably $C_1$-$C_4$ alkyl, wherein the alkyl moiety may be substituted with one or more halogen atoms or (halo)alkoxy moieties, more preferably $R^3$ is $C_1$-$C_2$ alkyl, wherein the alkyl moiety may be substituted with one or more halogen atoms or (halo)alkoxy moieties. Preferred moieties comprising an imine moiety include guanidine and amidine, wherein one of the nitrogen atoms is substituted to form the connection with the amide nitrogen atom via linker L.

$R^4$ is the substituent on the cationic nitrogen atom, which originates from formal protonation or alkylation of the amine or imine moiety. Thus, the compound according to the invention, in view of the presence of the cationic nitrogen atom and $X^-$, is a salt, preferably a pharmaceutically acceptable salt. Pharmaceutically acceptable salts are those salts which can be administered as drugs or pharmaceuticals to humans and/or animals. The pharmaceutically acceptable salts of the amine or imine moiety of the compound according to the invention are known to those skilled in the art, and originate from formal treatment of the compound with an acid or an alkylating agent. Suitable acids include organic acids or inorganic acids. Examples of inorganic acids include, but are not limited to, hydrochloric acid (HCl), hydrobromic acid (HBr), hydroiodic acid (HI), sulfuric acid ($H_2SO_4$), nitric acid ($HNO_3$), trifluoroacetic acid (TFAH or $CF_3CO_2H$) and phosphoric acid ($H_3PO_4$). Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids and salicylic acid. When an acid as exemplified here is used to formally prepare the salt, $R^4$ is hydrogen, and the type of acid determines counter ion X. Alternatively, the salt can be formed by formal treatment with an alkylating agent. Suitable alkylating agents include, but are not limited to, $C_1$-$C_6$ alkyl halides (such as methyl iodide, ethyl iodide, propyl iodide, butyl chloride, butyl fluoride, butyl bromide), dimethyl sulfate, dimethyl carbonate, methyl triflate, methyl fluorosulfonate, methyl chlorosulfonate, methyl methanesulfonate en methyl benzenesulfonate. The salt may be prepared by actual treatment of the non-salt compound with an acid or alkylation agent, as indicated above, or via other means known in the art and/or exemplified further below.

$R^4$ is selected from hydrogen (H) or $C_1$-$C_6$ alkyl, wherein the alkyl moiety may be substituted with one or more halogen atoms or (halo)alkoxy moieties, preferably $R^4$ is H or $C_1$-$C_4$ alkyl, wherein the alkyl moiety may be substituted with one or more halogen atoms or (halo)alkoxy moieties, more preferably $R^4$ is H or $C_1$-$C_2$ alkyl, wherein the alkyl moiety may be substituted with one or more halogen atoms or (halo)alkoxy moieties. Halogen atoms include fluorine (F), chlorine (Cl), bromine (Br), iodine (I), and astatine (At), preferably the halogen atom is fluorine (F). Preferred alkoxy moieties include methoxy and ethoxy. In haloalkoxy moieties, at least one hydrogen atom of an alkoxy moiety is replaced by a halogen atom, preferably by F. Suitable moieties for $R^4$ include, preferably are limited to, H, methyl (Me), trifluoromethyl ($CF_3$), ethyl (Et), isopropyl (iPr), cyclopropyl (-cPr), methylene cyclopropyl (—$CH_2$cPr), n-propyl (n-Pr), 2,2,2-trifluoroethyl (—$CH_2CF_3$), methoxymethyl (—CH$_2$OCH$_3$). Even more preferably R$^4$ is H or methyl (Me), most preferably R$^4$ is H. X can be any anion, preferably a physiologically or pharmaceutically acceptable anion, more preferably a monovalent anion. X is preferably selected from F, Cl, Br, I, HSO$_4$, NO$_3$, TFA (CF$_3$CO$_2$), formate, acetate, propionate, glycolate, pyruvate, oxalate, maleate, malonate, succinate, fumarate, tartarate, citrate, benzoate, cinnamate, mandelate, sulfonate and salicylate. Preferably, X is Cl, I, TFA or formate, more preferably Cl, I or TFA, most preferably X is Cl. When the cationic nitrogen atom originates from formal protonation, this protonation is preferably accomplished with hydrogen chloride (HCl), trifluoroacetic acid (TFAH or CF$_3$CO$_2$H) or formic acid (HCOOH), more preferably with HCl or TFAH. Formal methylation is preferably accomplished with methyl iodide (MeI). Thus, in a preferred embodiment, R$^4$=Me when X$^-$=I$^-$, and R$^4$=H when X$^-$=Cl$^-$, TFA$^-$ or formate.

Apart from the occurrences as described here below, R$^1$ and R$^2$ are each independently selected from hydrogen (H) or C$_1$-C$_6$ alkyl. Preferably, R$^1$ is H or C$_1$-C$_2$ alkyl, more preferably R$^1$ is H or methyl (Me), most preferably R$^1$ is H. Preferably, R$^2$ is H or C$_1$-C$_2$ alkyl, more preferably R$^2$ is H or methyl (Me), most preferably R$^2$ is Me.

In one embodiment, the amide nitrogen atom is connected to the cationic nitrogen atom via a second linker. This second linker is defined by joining together R$^1$ on the amide nitrogen atom and R$^2$ on the cationic nitrogen atom. Thus, the amide nitrogen atom, the cationic nitrogen atom, the first linker and the second linker together form a cyclic structure, preferably a 4-10-membered cyclic structure, more preferably a 5-8-membered cyclic structure, most preferably a 6-membered cyclic structure. In a preferred embodiment, the second linker is a —CH$_2$—CH$_2$— or —CH$_2$—CH$_2$—CH$_2$— bridge, most preferably a —CH$_2$—CH$_2$— bridge, wherein two or three, preferably two, carbon atoms are present between the amide nitrogen atom and the cationic nitrogen atom.

In another embodiment, the amide nitrogen atom is connected to a backbone atom of the linker, thereby forming a cyclic structure, preferably a 4-10-membered cyclic structure, more preferably a 5-8-membered cyclic structure, most preferably a 6-membered cyclic structure. The backbone atom of the linker to which the nitrogen atom is connected in this respect has a sub stituent R", which is joined together with R$^1$ on the amide nitrogen atom. In this embodiment, the cationic nitrogen atom is not included in the cyclic structure, but instead only part of the backbone of the linker is included. In a preferred embodiment, this connection between the amide nitrogen atom and a backbone atom of the linker is a —CH$_2$—CH$_2$— or —CH$_2$—CH$_2$—CH$_2$— bridge, most preferably a —CH$_2$—CH$_2$— bridge, wherein two or three, preferably two, carbon atoms are present between the amide nitrogen atom and the backbone atom of the linker.

In another embodiment, the cationic nitrogen atom is connected to a backbone atom of the linker, thereby forming a cyclic structure, preferably a 4-10-membered cyclic structure, more preferably a 5-8-membered cyclic structure, most preferably a 6-membered cyclic structure. The backbone atom of the linker to which the nitrogen atom is connected in this respect has a sub stituent R$^{2'}$, which is joined together with R$^2$ on the cationic nitrogen atom. In this embodiment, the amide nitrogen atom is not included in the cyclic structure, but instead only part of the backbone of the linker is included. In a preferred embodiment, this connection between the cationic nitrogen atom and a backbone atom of the linker is a —CH$_2$—CH$_2$— or —CH$_2$—CH$_2$—CH$_2$— bridge, most preferably a —CH$_2$—CH$_2$— bridge, wherein two or three, preferably two, carbon atoms are present between the cationic nitrogen atom and the backbone atom of the linker. It is also possible that a connection exists between R$^1$ on the amide nitrogen atom and an R$^{1'}$ substituent on the linker and between R$^2$ on the cationic nitrogen atom and an R$^{2'}$ substituent on the linker.

In a preferred embodiment, the solubility of the compound of the invention in water, expressed as log(P$_{ow}$) is between 2.0 and 5.0, preferably between 2.5 and 4.5, more preferably between 3.0 and 4.0. Log(P$_{ow}$), the logarithm of the partition coefficient between 1-octanol and water, is a well-known measure of water solubility. Compounds having a log(P$_{ow}$) value between 3 and 4 are ideally balanced between sufficient water solubility for preparation of aqueous solutions or suspensions and sufficient lipophilicity to ensure efficient transport of the compound over the cellular membrane. The skilled person will appreciate how to determine which combinations of L, R$^1$, R$^2$, R$^3$, R$^4$ and X as defined above afford a compound having a log(P$_{ow}$) value between 3 and 4. Suitable tests to define the log(P$_{ow}$) value of a compound are well-known to the skilled person, and include but are not limited to the shake-flask method, ITIES, the droplet method or using HPLC. The log(P$_{ow}$) of a compound can also be predicted using QSPR algorithms.

Appropriate linkers L to connect the amide nitrogen atom to the cationic nitrogen atom, are linkers preferably comprising 1 to 10 optionally substituted backbone atoms more preferably comprising 1 to 8 optionally substituted backbone atoms. L can thus comprise 1, 2, 3, 4, 5, 6, 7, 8, 9 or 10 optionally substituted backbone atoms. Herein, backbone atoms are those atoms which make up the shortest chain between the amide nitrogen atom and the cationic nitrogen atom. The backbone may be a linear structure, but may also be part of a cyclic structure. When the backbone is part a cyclic structure, the backbone is defined as the shortest chain between the amide nitrogen atom and the cationic nitrogen atom. In such instances, one of the backbone atoms comprises a substituent R$^5$, and one of the backbone atoms comprises a substituent R$^{5'}$, preferably two different backbone atoms comprise the substituents R$^5$ and R$^{5'}$, wherein R$^5$ and R$^{5'}$ are joined to form a cyclic structure, preferably a 4-10-membered cyclic structure, more preferably a 5-8-membered cyclic structure, most preferably a 6-membered cyclic structure. In this embodiment, the amide nitrogen atom and the cationic nitrogen atom are not included in the cyclic structure, but instead only part of the backbone of the linker is included. In a preferred embodiment, this connection between the backbone atom(s) of the linker, bearing the R$^5$ and R$^{5'}$ substituents, is a —(CH$_2$)$_n$— bridge, wherein n=1-6, preferably a —CH$_2$—CH$_2$— or —CH$_2$—CH$_2$—CH$_2$— bridge, wherein one to six, preferably two or three, carbon atoms are present between the substituted backbone atom(s) of the linker.

In a preferred embodiment, the backbone atoms are selected from carbon, nitrogen and oxygen, preferably from carbon and nitrogen. Such a backbone according to this preferred embodiment may be identified as C$_{n-m}$N$_m$, wherein n designates the total number of atoms in the backbone, and m the number of nitrogen atoms in the backbone. Each of n and m is a non-negative integer. Suitable linkers have n=1-10 and m=0-4, preferably n=2-7 and m=0-3, more preferably n=4-7 and m=0-2. Especially preferred linkers have a backbone identified as wherein n=2 and m=0 (C$_2$); n=5 and m=1 (C$_4$N); n=3 and m=0 (C$_3$); n=4 and m=1 (C$_3$N); n=7 and m=2 (C$_5$N$_2$); n=4 and m=0 (C$_4$); n=6 and m=1 (C$_5$N); or n=5 and m=0 (C$_5$). Most preferably, all backbone atoms are carbon atoms (m=0).

To fulfill their valence requirements, the carbon and nitrogen backbone atoms of the linker may bear hydrogen atoms, may be substituted, or double or triple bonds may be present between adjacent backbone atoms, as will be understood by the skilled person. In the context of the invention, hydrogen is not regarded a substituent. Whenever an oxygen atom is present as backbone atom in the linker, the skilled person will understand that the oxygen backbone atom bears no hydrogen atoms, substituents or double or triple bonds. Triple bonds may be present between two carbon atoms of the backbone. The backbone atoms, together with the hydrogen atoms and/or the substituents, constitute the linker. In the context of the present invention, "optionally substituted" is used to indicate that a (backbone) atom may bear one or more substituents, or may bear no substituents and 0-3 hydrogen may be present instead, to fulfill the valence requirements of said (backbone) atom.

Suitable substituents include but are not limited to halogen, $NH_2$, $NHR^6$, $N(R^6)_2$, $NHNH_2$, $N_3$, $NHC(=O)R^6$, $NHC(=O)NHR^6$, $NHC(=O)NH_2$, $NHC(=O)OR^6$, OH, $OR^6$, $OC(=O)R^6$, $R^6$ (e.g. alkyl, cycloalkyl), aralkyl, alkenyl, alkynyl, aryl, heteroaryl, $OC(=O)OR^6$, $OC(=O)NHR^6$, $O(SO_2)R^6$, $O(SO_2)OH$, $O(PO_2)OH$, SH, $SR^6$, $C(=O)R^6$, alkyl-$NH_2$, alkyl-OH, alkyl-SH, $C(=O)CF_3$, $C(=O)OR^6$, $C(=O)OH$, $C(=O)H$, $C(=O)OR^6$, $C(=O)NH_2$, $C(=O)NMe_2$, $C(=O)N(R^6)_2$, $C(=S)NH_2$—$C(=S)SH$, CN, NC, CNO, ONC, OCN, SCN, SNC, CNS, $S(=O)R^6$, $S(=O)_2R^6$, $S(=O)_2(OH)$, $P(=O)(OH)_2$ or $P(=O)(OH)(OR^6)$. Atoms having two or more remaining valencies, such as carbon backbone atoms, may bear a double bonded substituent, such as oxo (=O), imino (=NH or =$NR^6$), thioxo (=S), alkylidene (=$CH_2$ or =$CHR^6$ or =$C(R^6)_2$). In addition, two substituents on the same atom or on different atoms may be joined to form cyclic structures. If two substituents on a single backbone atom are joined in a cyclic structure, this cyclic structure may be regarded as being connected via a spino junction to the backbone. If two substituents on different backbone atoms are joined in a cyclic structure, part of this cyclic structure is (part of) the backbone, and the backbone is considered to be the shortest chain of atoms between the amide nitrogen atom and the cationic nitrogen atom. As further indicated below, a cyclic structure may also be formed by joining one substituent on a backbone atom with $R^1$ on the amide nitrogen atom or with $R^2$ on the cationic nitrogen atom. The cyclic structures formed as such may be all-carbon or may comprise 0-3 heteroatoms (e.g. N, O, S and/or P), and may comprise 0-3 double bonds. All atoms in these cyclic structures may optionally be substituted. Examples of suitable cyclic structures are optionally substituted cycloalkyl, optionally substituted cycloheteroalkyl, optionally substituted aryl or optionally substituted heteroaryl. Here above, each $R^6$ is independently an alkyl moiety, preferably a $C_1$-$C_6$ alkyl moiety, more preferably a $C_1$-$C_2$ alkyl moiety. Within $R^6$, one or more $CH_2$ moieties may each independently be replaced by one of O, S or NH, and/or one or more CH moieties may be replaced by N.

In the context of the present invention, the term "alkyl" refers to saturated aliphatic groups including straight-chain, branched-chain, cyclic groups, and combinations thereof, having the number of carbon atoms specified, or if no number is specified, preferably having up to 12 carbon atoms. "Straight-chain alkyl" or "linear alkyl" group refers to alkyl groups that are neither cyclic nor branched, commonly designated as "n-alkyl" groups. One subset of alkyl groups is $C_1$-$C_6$ alkyl, which include groups such as methyl, ethyl, n-propyl, isopropyl, butyl, n-butyl, isobutyl, sec-butyl, t-butyl, pentyl, n-pentyl, hexyl, cyclopropyl, cyclobutyl, cyclopentyl, cyclohexyl, and any other alkyl group containing between one and six carbon atoms, where the $C_1$-$C_6$ alkyl groups can be attached via any valence on the $C_1$-$C_6$ alkyl groups.

Preferred substituents of the backbone atoms are alkyl, such as methyl (Me or $CH_3$), carboxy (—C(=O)OH), oxo (=O), primary amino (—$NH_2$).

Preferred linkers are identified here below as $L^1$ to $L^{26}$:

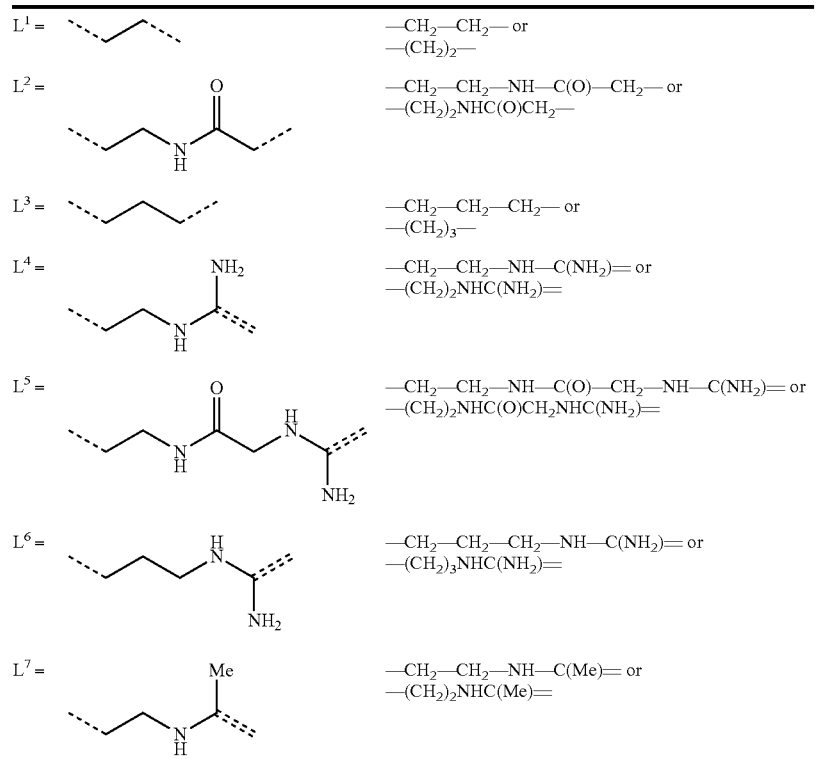

-continued

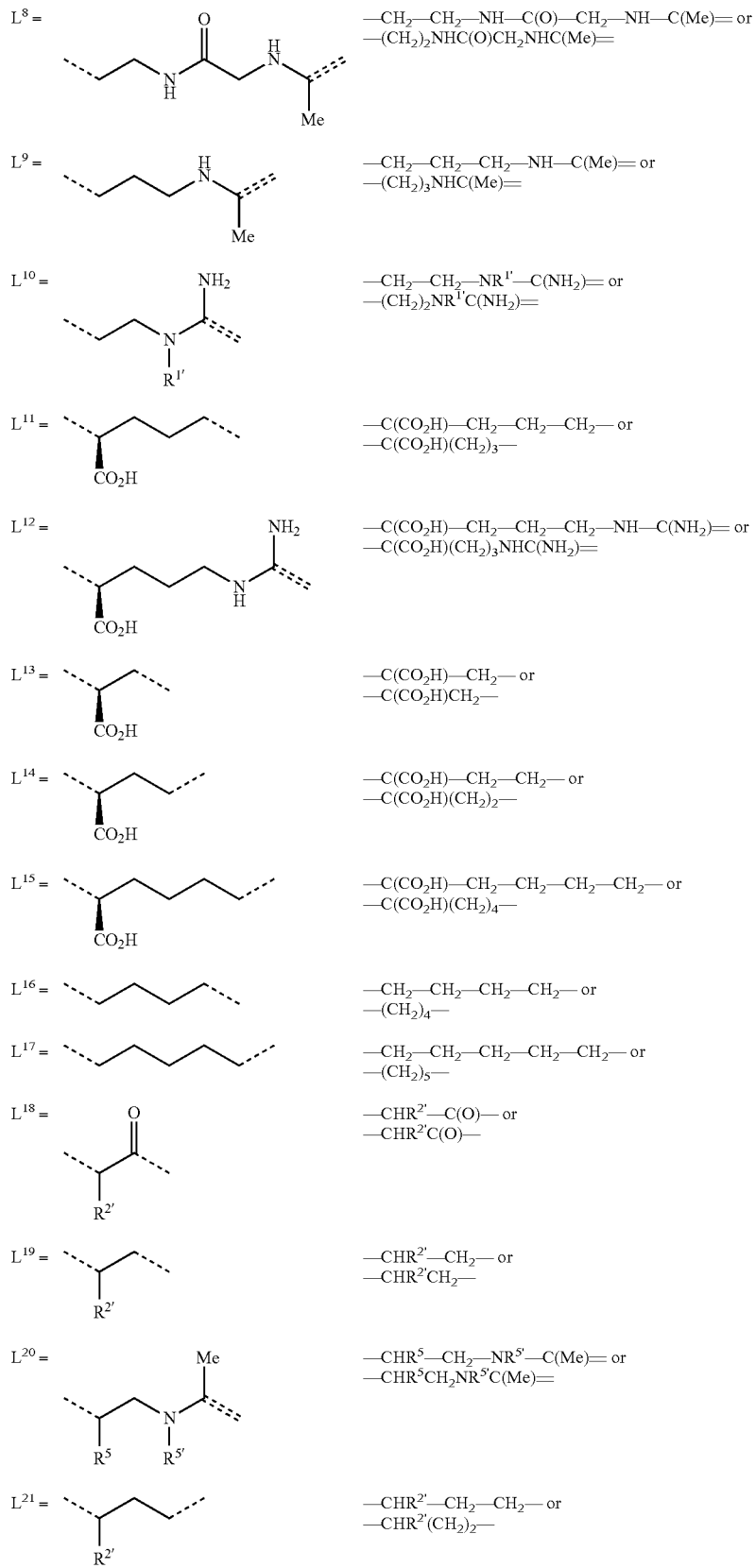

L⁸ = —CH₂—CH₂—NH—C(O)—CH₂—NH—C(Me)= or
—(CH₂)₂NHC(O)CH₂NHC(Me)=

L⁹ = —CH₂—CH₂—CH₂—NH—C(Me)= or
—(CH₂)₃NHC(Me)=

L¹⁰ = —CH₂—CH₂—NR¹'—C(NH₂)= or
—(CH₂)₂NR¹'C(NH₂)=

L¹¹ = —C(CO₂H)—CH₂—CH₂—CH₂— or
—C(CO₂H)(CH₂)₃—

L¹² = —C(CO₂H)—CH₂—CH₂—CH₂—NH—C(NH₂)= or
—C(CO₂H)(CH₂)₃NHC(NH₂)=

L¹³ = —C(CO₂H)—CH₂— or
—C(CO₂H)CH₂—

L¹⁴ = —C(CO₂H)—CH₂—CH₂— or
—C(CO₂H)(CH₂)₂—

L¹⁵ = —C(CO₂H)—CH₂—CH₂—CH₂—CH₂— or
—C(CO₂H)(CH₂)₄—

L¹⁶ = —CH₂—CH₂—CH₂—CH₂— or
—(CH₂)₄—

L¹⁷ = —CH₂—CH₂—CH₂—CH₂—CH₂— or
—(CH₂)₅—

L¹⁸ = —CHR²'—C(O)— or
—CHR²'C(O)—

L¹⁹ = —CHR²'—CH₂— or
—CHR²'CH₂—

L²⁰ = —CHR⁵—CH₂—NR⁵'—C(Me)= or
—CHR⁵CH₂NR⁵'C(Me)=

L²¹ = —CHR²'—CH₂—CH₂— or
—CHR²'(CH₂)₂—

-continued

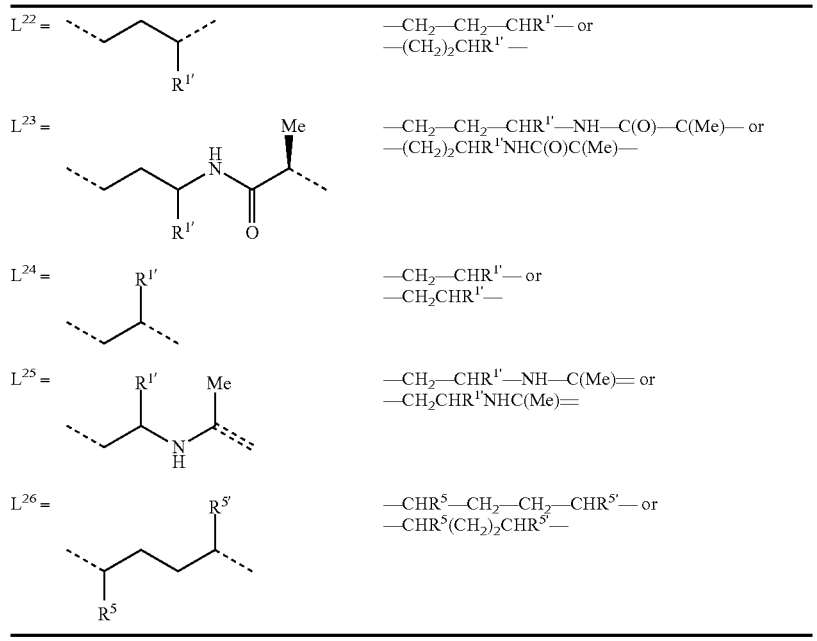

| | | |
|---|---|---|
| $L^{22}$ = | (structure with $R^{1'}$) | —$CH_2$—$CH_2$—$CHR^{1'}$— or —$(CH_2)_2CHR^{1'}$— |
| $L^{23}$ = | (structure with Me, NH, $R^{1'}$, O) | —$CH_2$—$CH_2$—$CHR^{1'}$—NH—C(O)—C(Me)— or —$(CH_2)_2CHR^{1'}NHC(O)C(Me)$— |
| $L^{24}$ = | (structure with $R^{1'}$) | —$CH_2$—$CHR^{1'}$— or —$CH_2CHR^{1'}$— |
| $L^{25}$ = | (structure with $R^{1'}$, Me, NH) | —$CH_2$—$CHR^{1'}$—NH—C(Me)= or —$CH_2CHR^{1'}NHC(Me)$= |
| $L^{26}$ = | (structure with $R^{5'}$, $R^5$) | —$CHR^5$—$CH_2$—$CH_2$—$CHR^{5'}$— or —$CHR^5(CH_2)_2CHR^{5'}$— |

Herein, the dashed bond at the left side of each of the structures for $L^1$ to $L^{26}$ indicates the bond between the linker and the amide nitrogen atom, and the dashed bond at the right side of each of the structures for $L^1$ to $L^{26}$ indicates the bond between the linker and the cationic nitrogen atom. The linkers depicted as chemical formulas are oriented in the same direction, i.e. the pendant bond at the left side of each of the chemical formulas for $L^1$ to $L^{26}$ indicates the bond between the linker and the amide nitrogen atom, and the dashed bond at the right side of each of the chemical formulas for $L^1$ to $L^{26}$ indicates the bond between the linker and the cationic nitrogen atom.

Each occurrence of $R^{1'}$ is a bridge between the linker and the amide nitrogen atom, wherein $R^{1'}$ is joined with $R^1$ via said bridge, thus forming a 4-10-membered cyclic structure, preferably a 5-8-membered cyclic structure, most preferably a 6-membered cyclic structure, which is built up from the amide nitrogen atom, 1-4 atoms of the backbone of the linker, and 1-4 atoms which make up the bridge joining $R^1$ and $R^{1'}$. Likewise, each occurrence of $R^{2'}$ is a bridge between the linker and the cationic nitrogen atom, wherein $R^{2'}$ is joined with $R^2$ via said bridge, thus forming a 4-10-membered cyclic structure, preferably a 5-8-membered cyclic structure, most preferably a 6-membered cyclic structure, which is built up from the cationic nitrogen atom, 1-4 atoms of the backbone of the linker, and 1-4 atoms which make up the bridge joining $R^2$ and $R^{2'}$. Likewise, each occurrence of $R^5$ and $R^{5'}$ is a bridge between one backbone atom of the linker, bearing $R^5$, and another backbone atom of the linker, bearing $R^{5'}$, wherein $R^{5'}$ is joined with $R^5$ via said bridge, thus forming a 4-10-membered cyclic structure, preferably a 5-8-membered cyclic structure, most preferably a 6-membered cyclic structure, which is built up from 2-5 atoms of the backbone of the linker, and 1-5 atoms which make up the bridge joining $R^5$ and $R^{5'}$. Thus, in linkers $L^{10}$, $L^{22}$, $L^{23}$, $L^{24}$ and $L^{25}$, $R^{1'}$ is joined to $R^1$ via a bridge, preferably a —$CH_2$—$CH_2$— or —$CH_2$—$CH_2$—$CH_2$— bridge, more preferably a —$CH_2$—$CH_2$— bridge. Thus, in a compound comprising linker $L^{10}$, wherein $R^{1'}$ and $R^1$ are joined via a —$CH_2$—$CH_2$— bridge, the amide nitrogen atom is embedded in a six-membered cyclic structure, which is built up from the amide nitrogen atom, two carbon atoms and one nitrogen atom of the backbone of the linker, and two more carbon atoms which make up the bridge of $R^1$ and $R^{1'}$. This —$CH_2CH_2$— bridge between the amide nitrogen atom and the central nitrogen atom in the backbone of linker $L^{10}$ may be represented as $L^1$. Likewise, in linkers $L^{18}$, $L^{19}$ and $L^{21}$, $R^{2'}$ is joined to $R^2$ via a bridge, preferably a —$CH_2$—$CH_2$— or —$CH_2$—$CH_2$—$CH_2$— bridge, more preferably a —$CH_2$—$CH_2$—$CH_2$— bridge. Likewise, in linker $L^{20}$ and $L^{26}$, $R^{5'}$ is joined to $R^5$ via a bridge, preferably a —$CH_2$—$CH_2$— or —$CH_2$—$CH_2$—$CH_2$— bridge, more preferably a —$CH_2$—$CH_2$— bridge.

Linkers $L^{11}$, $L^{12}$, $L^{13}$, $L^{15}$, $L^{18}$ (as long as $R^2$—$R^{2'}$ is not —C(O)—), $L^{19}$ (as long as $R^2$—$R^{2'}$ is not —$CH_2$—), $L^{20}$ (as long as $R^5$—$R^{5'}$ is not —$CH_2$—), $L^{21}$ (as long as $R^2$—$R^{2'}$ is not —$CH_2$—$CH_2$—), $L^{22}$ (as long as $R^1$—$R^{1'}$ is not —$CH_2$—$CH_2$—), $L^{23}$ (as long as $R^1$—$R^{1'}$ is not —$CH_2$—$CH_2$—), $L^{24}$ (as long as $R^1$—$R^{1'}$ is not —$CH_2$—) and $L^{25}$ (as long as $R^1$—$R^{1'}$ is not —$CH_2$—) comprise an additional stereocenter. The stereoisomer, when indicated in the structures of those linkers, above is meant as illustrative, not as limiting. As indicated further above, each stereocenter present in the compounds according to the invention may individually be present in each of its stereoisomeric forms, either S or R, or as a mixture of both isomers in any ratio. Linker $L^{26}$ comprises a disubstituted cycloalkyl moiety, preferably a disubstituted cyclohexyl moiety, and may thus occur in either the cis-form or the trans-form, preferably in the trans-form.

In one embodiment of the invention, especially preferred linkers are $L^5$, $L^8$, $L^{11}$ and $L^{12}$, even more preferred linkers are $L^8$ and $L^{11}$, and the most preferred linker according to this embodiment of the invention is $L^{11}$. Additional preferred linkers according to this embodiment are $L^{16}$, $L^{17}$, $L^{19}$, $L^{21}$ and $L^{26}$, more preferably $L^{16}$ and $L^{19}$. Thus, according to this embodiment, the preferred linkers are $L^5$, $L^8$, $L^{11}$, $L^{12}$, $L^{16}$, $L^{17}$, $L^{19}$, $L^{21}$ and $L^{26}$, more preferably $L^8$, $L^{12}$, $L^{16}$, $L^{17}$, $L^{19}$, $L^{21}$ and $L^{26}$, most preferably $L^{16}$ and $L^{19}$. Preferably, $L^{19}$ is combined with $R^2$—$R^{2'}$=$L^1$ or $L^3$, most preferably with $R^2$—$R^{2'}$=$L^3$. Preferably, $L^{21}$ is combined with $R^2$—$R^{2'}$=$L^1$ or $L^3$, most preferably with $R^2$—$R^{2'}$=$L^1$. Preferably, $L^{26}$ is combined with $R^5$—$R^{5'}$=$L^1$ or $L^3$, more preferably with $R^5$—$R^{5'}$=$L^1$, most preferably with $R^5$—$R^{5'}$=$L^1$, wherein the cyclohexyl is trans-1,4-disubstituted. Especially preferred is the combination of linker $L^{19}$ with $R^2$—$R^{2'}$=$L^3$ and $R^3$=H, Me, Et, iPr, $CH_2OCH_3$ or $CH_2CF_3$, more preferably $R^3$=Me, Et, iPr or $CH_2CF_3$.

In another embodiment of the invention, especially preferred linkers are $L^7$ and $L^1$, and an even more preferred linker is $L^7$.

Preferred compounds according to the invention are identified here below as compounds A to O, which are defined by general formula (I), wherein:

for compound A: L=$L^1$, $R^1$—$R^2$=$L^1$, $R^3$=H, $R^4$=H, $X^-$=$Cl^-$;
for compound B: L=$L^1$, $R^1$=H, $R^2$=H, $R^3$=H, $R^4$=H; $X^-$=$Cl^-$;
for compound C: L=$L^2$, $R^1$=H, $R^2$=H, $R^3$=H, $R^4$=H; $X^-$=$Cl^-$;
for compound D: L=$L^3$, $R^1$=H, $R^2$=H, $R^3$=H, $R^4$=H; $X^-$=$Cl^-$;
for compound E: L=$L^4$, $R^1$=H, $R^2$=H, $R^3$=absent, $R^4$=H; $X^-$=$TFA^-$;
for compound F: L=$L^5$, $R^1$=H, $R^2$=H, $R^3$=absent, $R^4$=H; $X^-$=$TFA^-$;
for compound G: L=$L^6$, $R^1$=H, $R^2$=H, $R^3$=absent, $R^4$=H; $X^-$=$TFA^-$;
for compound H: L=$L^3$, $R^1$=H, $R^2$=Me, $R^3$=Me, $R^4$=Me; $X^-$=F;
for compound I: L=$L^1$, $R^1$=H, $R^2$=Me, $R^3$=Me, $R^4$=Me; $X^-$=F;
for compound J: L=$L^7$, $R^1$=H, $R^2$=H, $R^3$=absent, $R^4$=H; $X^-$=$Cl^-$;
for compound K: L=$L^8$, $R^1$=H, $R^2$=H, $R^3$=absent, $R^4$=H; $X^-$=$Cl^-$;
for compound L: L=$L^9$, $R^1$=H, $R^2$=H, $R^3$=absent, $R^4$=H; $X^-$=$Cl^-$;
for compound M: L=$L^{10}$, $R^1$—$R^{1'}$=$L^1$, $R^2$=H, $R^3$=absent, $R^4$=H; $X^-$=TFA;
for compound N: L=$L^{11}$, $R^1$=H, $R^2$=H, $R^3$=H, $R^4$=H; $X^-$=$Cl^-$;
for compound O: L=$L^{12}$, $R^1$=H, $R^2$=H, $R^3$=absent, $R^4$=H; $X^-$=$Cl^-$.

Additional preferred compounds according to the invention are identified here below as compounds P to AH, which are defined by general formula (I), wherein:

for compound P: L=$L^{13}$, $R^1$=H, $R^2$=H, $R^3$=H, $R^4$=H; $X^-$=$Cl^-$;
for compound Q: L=$L^{14}$, $R^1$=H, $R^2$=H, $R^3$=H, $R^4$=H; $X^-$=$Cl^-$;
for compound R: L=$L^{15}$, $R^1$=H, $R^2$=H, $R^3$=H, $R^4$=H; $X^-$=$Cl^-$;
for compound S: L=L", $R^1$=H, $R^2$=Me, $R^3$=Me, $R^4$=H; $X^-$=$Cl^-$;
for compound T: L=$L^{16}$, $R^1$=H, $R^2$=H, $R^3$=H, $R^4$=H; $X^-$=$Cl^-$;
for compound U: L=$L^{17}$, $R^1$=H, $R^2$=H, $R^3$=H, $R^4$=H; $X^-$=$Cl^-$;
for compound V: L=$L^{16}$, $R^1$=H, $R^2$=Me, $R^3$=Me, $R^4$=H; $X^-$=$Cl^-$;
for compound W: L=$L^{18}$, $R^1$=H, $R^2$—$R^2$=$L^3$, $R^3$=H, $R^4$=H; $X^-$=$Cl^-$;
for compound X: L=$L^{19}$, $R^1$=H, $R^2$—$R^{2'}$=$L^3$, $R^3$=H, $R^4$=H; $X^-$=$Cl^-$;
for compound Y: L=$L^{20}$, $R^1$=H, $R^2$—$R^5$=$L^3$, $R^3$=absent, $R^4$=H; $X^-$=$Cl^-$;
for compound Z: L=$L^{21}$, $R^1$=H, $R^2$—$R^{2'}$=$L^1$, $R^3$=H, $R^4$=H; $X^-$=$Cl^-$;
for compound AA: L=$L^{22}$, $R^1$—$R^{1'}$=$L^1$, $R^2$=H, $R^3$=H, $R^4$=H; $X^-$=$Cl^-$;
for compound AB: L=$L^{23}$, $R^1$—$R^{1'}$=$L^1$, $R^2$=H, $R^3$=H, $R^4$=H; $X^-$=$Cl^-$;
for compound AC: L=$L^{24}$, $R^1$—$R^{1'}$=$L^3$, $R^2$=H, $R^3$=H, $R^4$=H; $X^-$=$Cl^-$;
for compound AD: L=$L^{25}$, $R^1$—$R^{1'}$=$L^3$, $R^2$=H, $R^3$=absent, $R^4$=H; $X^-$=$Cl^-$;
for compound AE: L=$L^{26}$, $R^1$=H, $R^2$=H, $R^5$—$R^5$=$L^1$, $R^3$=H, $R^4$=H; $X^-$=$Cl^-$.
for compound AF: L=$L^{19}$, $R^1$=H, $R^2$=$L^3$, $R^3$=Me, $R^4$=H; $X^-$=$Cl^-$;
for compound AG: L=$L^{19}$, $R^1$=H, $R^2R^{2'}$=$L^1$, $R^3$=H, $R^4$=H; $X^-$=$Cl^-$;
for compound AH: L=$L^{21}$, $R^1$=H, $R^2R^{2'}$=$L^1$, $R^3$=Me, $R^4$=H; $X^-$=$HCOO^-$ In one embodiment, the compound of the invention is not compound D, and is preferably selected from the group consisting of compounds A to C and E to AH, more preferably from the group consisting of compounds A to C and E to P.

In one embodiment of the invention, especially preferred compounds are compounds F, K, N and O. Even more preferred compounds according to the invention are compounds K and N. The most preferred compound according to according to this embodiment of the invention the invention is compound N. Additional preferred compounds according to this embodiment are compounds U, V, T, X, Z, AE, AF, AG and AH, more preferably compound U, V, X, Z, AE, AF and AH, most preferably compound V, X and AF. Thus, according to this embodiment, the preferred compounds are F, K, N, O, U, V, T, X, Z, AE, AF, AG and AH, more preferably K, N, U, V, X, Z, AE, AF and AH, most preferably V, X and AF.

Compound F may have the R-configuration, the S-configuration or a mixture thereof, preferably compound F is a mixture of the R- and S-enantiomers, more preferably a racemic mixture. Compound K may have the R-configuration, the S-configuration or a mixture thereof, preferably compound K is a mixture of the R- and S-enantiomers, more preferably a racemic mixture. Compound N may have the R,R-configuration, R,S-configuration, S,R-configuration, the S,S-configuration or any mixture thereof, preferably compound N is a mixture of the R,S- and S,S-diastereomers, more preferably 1/1 (mol/mol) mixture. Compound O may have the R,R-configuration, R,S-configuration, S,R-configuration, the S,S-configuration or any mixture thereof, preferably compound O is a mixture of the R,S- and S,S-diastereomers more preferably 1/1 (mol/mol) mixture. Compound U may have the R-configuration, the S-configuration or a mixture thereof, preferably compound U has the R-configuration or the S-configuration. Compound V may have the R-configuration, the S-configuration or a mixture thereof, preferably compound V has the R-configuration. Compound T may have the R-configuration, the S-configuration or a mixture thereof, preferably compound T has the R-configuration or the S-configuration. Compound X may have the R,R-configuration, R,S-configuration, S,R-configuration, the S,S-configuration or any mixture thereof, preferably compound X has the S,R-configuration. Compound Z may have the R-configuration, the S-configuration or a mixture thereof, preferably compound Z is a mixture of the R- and S-enantiomers, more preferably a racemic mixture. Compound AE may have the R,trans-configuration, R,cis-configuration, S,trans-configuration, the S,cis-configuration or any mixture thereof, preferably compound AE has the R, trans-configuration or the S,trans-configuration. Compound AF may have the R,R-configuration, R,S-configuration, S,R-configuration, the S,S-configuration or any mixture thereof, preferably compound AF has the S,R-configuration. Compound AG may have the R,R-configuration, R,S-configuration, S,R-configuration, the S,S-configuration or any mixture thereof, preferably compound AG has the S,S-configuration or the S,R-configuration. Compound AH may have the R-configuration, the S-configuration or a mixture thereof, preferably compound AH has the S-configuration. Herein, the first designator (R or S) of the configuration is for the 2-position of the Trolox moiety, and in case an additional stereocenter is present in the compound according to the invention, the configuration of which is defined by the second designator. The most preferred compounds according to the invention are compound V in the R-configuration (R-V), compound X in the S,R-configuration (S,R-X) and compound AF in the S,R-configuration (S,R-AF).

In another embodiment of the invention, especially preferred compounds are compounds I and J, and an even more preferred compound is compound J. The invention also includes all stereoisomers and geometric isomers of the compounds, including diastereomers, enantiomers, and cis/trans (E/Z) isomers. The invention also includes mixtures of stereoisomers and/or geometric isomers in any ratio, including, but not limited to, racemic mixtures.

In one embodiment, the compound according to the invention is not the compound represented by formula (I), wherein:
L=—(CH$_2$)$_3$-(L$^3$), R$^1$=H, R$^2$=H, R$^3$=H, R$^4$=H; X=Cl; and/or
L=—(CH$_2$)$_2$—CHR$^1$—CH$_2$—NH—(CH$_2$)$_4$—, R$^1$—R$^{1'}$=—(CH$_2$)$_2$-(L$^1$), R$^2$=H, R$^3$=—(CH$_2$)$_2$—CH$_3$ (propyl), R$^4$=H; X=Cl; and/or
L=—(CH$_2$)$_3$-(L$^3$), R$^1$=H, R$^2$=H, R$^3$=H, R$^4$=H; X=TFA, which is in the S-configuration at the 2-position of the Trolox™-moiety.

The compounds can be administered in prodrug form. Prodrugs are derivatives of the compounds which are themselves relatively inactive, but which convert into the active compound when introduced into the subject in which they are used, by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, Design of Prodrugs (New York: Elsevier, 1985); in R. Silverman, The Organic Chemistry of Drug Design and Drug Action (Boston: Elsevier, 2004); in R. L. Juliano, Biological Approaches to the Controlled Delivery of Drugs (Annals of the New York Academy of Sciences, volume 507, New York: N.Y. Academy of Sciences, 1987); and in E. B. Roche, Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), published by The Academy in Washington, 1977.

The various compounds of the invention can be administered either as therapeutic or cosmetic agents in and of themselves, or as prodrugs which will convert to other effective substances in the body.

The compounds of the invention are useful for modulating mitochondrial morphology, i.e. either mitochondrial fragmentation or mitochondrial filamentation, and/or for modulating the expression (i.e. steady-state levels) of OXPHOS enzymes, such as complex I and complex II. Thus, in one aspect the invention relates to the use of the compounds of the invention in therapeutic and/or cosmetic methods for modulating at least one of mitochondrial morphology and expression of OXPHOS enzymes.

In one embodiment, the effect of the compounds of the invention includes one or more of induction of mitochondrial filamentation, prevention or reduction of mitochondrial fragmentation, and increased expression of OXPHOS enzymes. Preferred compounds for this embodiment are compounds wherein the linkers are L$^5$, L$^8$, L$^{11}$, L$^{12}$, L$^{16}$, L$^{17}$, L$^{19}$, L$^{21}$ and L$^{26}$, preferably in these compounds the linkers are L$^8$, L$^{11}$, L$^{16}$, L$^{17}$, L$^{19}$, L$^{21}$ and L$^{26}$, and most preferred the linkers according to this embodiment of the invention are L$^{16}$ and L$^{19}$. More specifically, preferred compounds of the invention having one or more of these effects are compounds F, K, N, O, U, V, T, X, Z, AE, AF, AG and AH. More preferred compounds according to the invention having one or more of these effects are compounds K, N U, V, X, Z, AE, AF and AH. The most preferred compounds according to according to this embodiment of the invention are compounds V, X and AF.

In another embodiment, the effect of the compounds of the invention includes one or more of reduced of mitochondrial filamentation, induction of mitochondrial fragmentation, and reduced expression of OXPHOS enzymes. Preferred compounds for this embodiment are compounds wherein the linkers are L$^7$ and L$^1$, and an even more preferred the linker is L$^7$. More specifically, preferred compounds of the invention having one or more of these effects are compounds I and J, and an even more preferred compound having one or more of these effects is compound J.

In another aspect, the invention relates to a compound of the invention as herein defined above for use as a medicament. The medicament can be used for both medical (human) as well as veterinary (animal) applications.

In a further aspect, the invention relates to a method of treating, preventing, or suppressing symptoms associated with a mitochondrial disorder or with a condition associated with mitochondrial dysfunction, the method comprising administering to a subject an effective amount of one or more compounds of the invention as herein defined above. Alternatively, the invention relates to a compound of the invention as herein defined above, for use in a method of treating, preventing, or suppressing symptoms associated with a mitochondrial disorder or with a condition associated with mitochondrial dysfunction. The methods of the invention, preferably comprise administering to a subject an effective amount of one or more compounds of the invention as herein defined above, and an acceptable carrier, excipient or vehicle, preferably a pharmaceutically or physiologically acceptable carrier, excipient or vehicle.

Preferred compounds of the invention for treating a mitochondrial disorder and/or a condition associated with mitochondrial dysfunction are compounds of which the effect includes one or more of induction of mitochondrial filamentation, prevention or reduction of mitochondrial fragmentation, and increased expression of OXPHOS enzymes, as defined herein above.

In the methods of the invention, the mitochondrial disorder and/or the condition associated with mitochondrial dysfunction preferably is a condition characterised by an OXPHOS deficiency. Every cell needs energy. Shortage of energy therefore affects the activity of every cell. Thus in principle every cell is affected by a sub-optimal amount of one or more of the OXPHOS complexes. However, the actual amount that is sub-optimal varies from cell to cell. Cells that have a relatively high energy consumption such as brain and muscle cells typically require a higher amount of OXPHOS system complexes than cells that have a low energy consumption, such as resting T-cells. Thus, the cells that are affected by said deficiency associated with an oxidative phosphorylation deficiency are typically, but not necessarily muscle cells or brain cells. Mitochondrial disorders are pleiotropic in their clinical manifestation. Various tissues can be affected like for instance pancreas, heart, liver, eye, inner ear, blood, colon and kidney. In addition, also cells from non-clinically affected tissues like fibroblasts often show a mitochondrial defect. Cells affected by an OXPHOS deficiency can be treated and provided with a higher amount of OXPHOS complex by providing the cell with a compound of the invention. A cell is affected by an OXPHOS deficiency when the OXPHOS capacity is lower than normal (i.e. a comparable cell of the same species from a healthy individual). The capacity is typically lower over a prolonged period of time. Apart from being derived from an individual with an OXPHOS deficiency there are several methods to determine whether a cell has an OXPHOS deficiency, such test encompass but are not limited to oxygen consumption, ATP production capacity, and enzymatic activities of individual OXPHOS complexes (Chretien and Rustin J Inherit Metab Dis. 2003;_26_(2-3): 189-98). It has surprisingly been found that administration of a compound of the invention to a cell, results in higher amounts of OXPHOS complexes, (i.e. the mitochondria of the cells).

In the methods of the invention, the mitochondrial disorder preferably is a disorder selected from the group consisting of: Myoclonic epilepsy; Myoclonic Epilepsy with Ragged Red Fibers (MERRF); Leber's Hereditary Optic Neuropathy (LHON); neuropathy, ataxia and retinitis pigmentosa (NARP); Mitochondrial Myopathy, Encephalopathy, Lactacidosis, Stroke (MELAS); Leigh syndrome; Leigh-like syndrome; Dominant Optic atrophy (DOA); Kearns-Sayre Syndrome (KSS); Maternally Inherited Diabetes and Deafness (MIDD); Alpers-Huttenlocher syndrome; Ataxia Neuropathy spectrum; Chronic Progressive External Ophthalmoplegia (CPEO); Pearson syndrome; Mitochondrial Neuro-Gastro-Intestinal Encephalopathy (MNGIE); Sengers syndrome; 3-methylglutaconic aciduria, sensorineural deafness, encephalopathy and neuro-radiological findings of Leigh-like syndrome (MEGDEL); SURF1 Leigh syndrome; myopathy; mitochondrial myopathy; cardiomyopathy; and encephalomyopathy and isolated or combined oxidative phosphorylation disorders In the methods of the invention, the condition associated with mitochondrial dysfunction preferably is a condition selected from the group consisting of: Friedreich's Ataxia (FRDA); renal tubular acidosis; Parkinson's disease; Alzheimer's disease; amyotrophic lateral sclerosis (ALS); Huntington's disease; Barth syndrome (also known as 3-Methyl-glutaconic aciduria type II); macula degeneration, preferably age-related macula degeneration; developmental pervasive disorders; hearing loss, deafness; diabetes; ageing; adverse drug effects hampering (normal) mitochondrial function, including e.g. mitochondrial dysfunction caused by nucleoside analog reverse transcriptase inhibitors (NRTIs), certain antibiotics and anti-epileptic drugs; and ischemia and reperfusion injury, preferably ischemic reperfusion injury after acute myocardial infarction (AMI), after stroke, including perinatal stroke, after hemorrhagic shock, after intestinal ischemia, after emergency coronary surgery for failed percutaneous transluminal coronary angioplasty (PCTA), after vascular surgery with blood vessel cross clamping (e.g. of aorta, leading to skeletal muscle ischemia), after pancreatitis after manipulation of pancreatic or bile duct (ERCP), and/or after organ transplantation.

In the methods of the invention, "subject", "individual", or "patient" is understood to be an individual organism, preferably a vertebrate, more preferably a mammal, most preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. Because many of the mitochondrial disorders are inherited, genetic screening can be used to identify patients at risk of the disease. The compounds and methods of the invention can then be administered to asymptomatic patients at risk of developing the clinical symptoms of the disease, in order to suppress the appearance of any adverse symptoms. "Therapeutic use" of the compounds discussed herein is defined as using one or more of the compounds discussed herein to treat or suppress a disease, as defined above. An "effective amount" of a compound is an amount of a compound which, when administered to a subject, is sufficient to reduce or eliminate either one or more symptoms of a disease, or to retard the progression of one or more symptoms of a disease, or to reduce the severity of one or more symptoms of a disease, or to suppress the manifestation of a disease, or to suppress the manifestation of adverse symptoms of a disease. An effective amount can be given in one or more administrations.

Several readily measurable clinical markers are used to assess the metabolic state of patients with mitochondrial disorders. These markers can also be used as indicators of the efficacy of the therapy using the compounds if the invention, as the level of a marker is moved from the pathological value to the healthy value. These clinical markers include, but are not limited to, one or more of the energy biomarkers, such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; amino acids, in particular alanine, citrulline and proline either in whole blood, plasma, cerebrospinal fluid, organic acids in body fluids, FGF21 in serum and skeletal muscle, phosphocreatine levels, NADH (NADH+H$^+$) or NADPH (NADPH+H$^+$) levels; NAD or NADP levels; ATP levels; anaerobic threshold; reduced coenzyme Q ($CoQ^{red}$) levels; oxidized coenzyme Q ($CoQ^{ox}$ levels; total coenzyme Q ($CoQ^{tot}$) levels; oxidized cytochrome C levels; reduced cytochrome C levels; oxidized cytochrome C/reduced cytochrome C ratio; acetoacetate levels, beta-hydroxy butyrate levels, acetoacetate/betahydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment of the invention, the level of one or more energy biomarkers in a patient suffering from a mitochondrial disease, such as Friedreich's ataxia, Leber's hereditary optic neuropathy, dominant optic atrophy, Leigh syndrome, SURF1, MERRF, MELAS, or KSS, is improved to within two standard deviations of the average level in a healthy subject. In another embodiment of the invention, the level of one or more of these energy biomarkers in a patient suffering from a mitochondrial disease, such as Friedreich's ataxia, Leber's hereditary optic neuropathy, dominant optic atrophy, Leigh syndrome, SURF1, MERRF, MELAS, or KSS is improved to within one standard deviation of the average level in a healthy subject. Exercise intolerance can also be used as an indicator of the efficacy of a given therapy, where an improvement in exercise tolerance (i.e. a decrease in exercise intolerance) indicates efficacy of a given therapy.

Several metabolic biomarkers have already been used to evaluate efficacy of $CoQ_{10}$, and these metabolic biomarkers can be monitored as energy biomarkers for use in the methods of the current invention. Pyruvate, a product of the anaerobic metabolism of glucose, is removed by reduction to lactic acid in an anaerobic setting or by oxidative metabolism, which is dependent on a functional mitochondrial OXPHOS. Dysfunction of the OXPHOS may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7):695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4): 448-55 (1992)) and toxic mitochondrial myopathies (Chariot et al., Arthritis Rheum. 37(4):583-6 (1994)). Changes in the redox state of liver mitochondria can be investigated by measuring the arterial ketone body ratio (acetoacetate/3-hydroxybutyrate: AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2): 287-91 (1997); Honda et al., Leuk. Res. 24(6):461-8 (2000); Pilger et al., Free Radic. Res. 35(3):273-80 (2000); Kim et al., Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS ($^1$H-MRS) (Kaufmann et al., Neurology 62(8):1297-302 (2004)). Phosphorous MRS ($^{31}$P-MRS) has been used to demonstrate low levels of cortical phosphocreatine (PCr) (Matthews et al., Ann. Neurol. 29(4): 435-8 (1991)), and a delay in PCr recovery kinetics following exercise in skeletal muscle (Matthews et al., Ann. Neurol. 29(4):435-8 (1991); Barbiroli et al., J. Neurol. 242(7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V 02 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic acid (lactate) levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of NADH+H$^+$, NADPH+H$^+$, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, mt.3243A>G and mt.8344A>G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, NADH (NADH+H$^+$) or NADPH (NADPH+H$^+$) can be measured by a variety of fluorescent, enzymatic, or electrochemical techniques, e. g., the electrochemical assay described in US2005/0067303.

Oxygen consumption (v$O_2$ or VO2), carbon dioxide output (v$CO_2$ or VCO2), and respiratory quotient (VCO2/VO2): v$O_2$ is usually measured either while resting (resting v$O_2$) or at maximal exercise intensity (v$O_2$ max). Optimally, both values will be measured. However, for severely disabled patients, measurement of v$O_2$ max may be impractical. Measurement of both forms of v$O_2$ is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, reduced Cytochrome C, and ratio of oxidized Cytochrome C to reduced Cytochrome C: Cytochrome C parameters, such as oxidized cytochrome C levels (Cyt C$^{ox}$), reduced cytochrome C levels (Cyt C$^{red}$), and the ratio of oxidized cytochrome C/reduced cytochrome C ratio (Cyt C$^{ox}$)/(Cyt C$^{red}$), can be measured by in vivo near infrared spectroscopy. See, e. g., Rolfe, P., "In vivo near-infrared spectroscopy," Annu. Rev. Biomed. Eng. 2:715-54 (2000)

and Strangman et al., "Non-invasive neuroimaging using near-infrared light" Biol. Psychiatry 52:679-93 (2002).

Exercise tolerance/Exercise intolerance: Exercise intolerance is defined as "the reduced ability to perform activities that involve dynamic movement of large skeletal muscles because of symptoms of dyspnea or fatigue" (Pina et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e. g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q ($CoQ^{red}$) levels, oxidized coenzyme Q ($CoQ^{ox}$) levels, total coenzyme Q ($CoQ^{tot}$) levels, oxidized cytochrome C levels, reduced cytochrome C levels, oxidized cytochrome C/reduced cytochrome C ratio, acetoacetate levels, beta-hydroxy butyrate levels, acetoacetate/betahydroxy butyrate ratio, 8-hydroxy-2'-deoxyguanosine (8-OHdG) levels, and levels of reactive oxygen species are known in the art and can be used to evaluate efficacy of the compounds and methods of the invention. (For the purposes of the invention, modulation, normalization, or enhancement of energy biomarkers includes modulation, normalization, or enhancement of anaerobic threshold).

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods of the invention. RQ=respiratory quotient; BMR=basal metabolic rate; HR (CO)=heart rate (cardiac output); T=body temperature (preferably measured as core temperature); AT=anaerobic threshold; pH=blood pH (venous and/or arterial).

TABLE 1

| Site of dysfunction | Biochemical event | Measurable Energy Biomarker | Physical Effect |
| --- | --- | --- | --- |
| OXPHOS | ↑ NADH | Δ lactate, Δ lactate:pyruvate ratio, Δ acetoacetate:β-hydroxybutyrate ratio | Metabolic dyscrasia & fatigue |
| OXPHOS | ↑ NADH | Amino acids | Metabolic dyscrasia & fatigue |
| OXPHOS | ↑ NADH | Organic acids | Metabolic dyscrasia & fatigue |
| OXPHOS | ↑ NADH | FGF21 | Metabolic dyscrasia & fatigue |
| OXPHOS | ↓ $H^+$ gradient | Δ ATP | Organ dependent dysfunction |
| OXPHOS | ↓ Electron flux | Δ $VO_2$, RQ, BMR, ΔT, AT, pH | Metabolic dyscrasia & fatigue |
| Mitochondria & cytosol | ↓ ATP, ↓ $VO_2$ | Δ Work, ΔHR (CO) | Exercise intolerance |
| Mitochondria & cytosol | ↓ ATP | Δ PCr | Exercise intolerance |
| Respiratory Chain | ↓ Cyt $C^{Ox/Red}$ | Δ~700-900 nm (NIR spectroscopy) | Exercise intolerance |
| Intermediary metabolism | ↓ Catabolism | Δ $C^{14}$-labeled substrates | Metabolic dyscrasia & fatigue |
| Respiratory Chain | ↓ Electron flux | Δ Mixed venous $VO_2$ | Metabolic dyscrasia & fatigue |
| Mitochondria & cytosol | ↑ Oxidative stress | Δ Tocopherol & Tocotrienols, CoQ10 docosahexanoic acid | Uncertain |
| Mitochondria & cytosol | ↑ Oxidative stress | Δ $Glutathione^{red}$ | Uncertain |
| Mitochondria & cytosol | Nucleic acid oxidation | Δ 8-hydroxy 2-deoxy guanosine | Uncertain |
| Mitochondria & cytosol | Lipid oxidation | Δ Isoprostane(s), eicasanoids | Uncertain |
| Cell membranes | Lipid oxidation | Δ Ethane (breath) | Uncertain |
| Cell membranes | Lipid oxidation | Δ Malondialdehyde | Uncertain |

Treatment of a subject afflicted by a mitochondrial disease in accordance with the methods of the invention may result in the inducement of a reduction or alleviation of symptoms in the subject, e.g. to halt the further progression of the disorder.

Partial or complete suppression of the mitochondrial disease can result in a lessening of the severity of one or more of the symptoms that the subject would otherwise experience. For example, partial suppression of MELAS could result in reduction in the number of stroke-like or seizure episodes suffered.

Any one energy biomarker or any combination of the energy biomarkers described herein provide conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

Mitochondrial dysfunction is a common cause of inherited multisystem disease that often involves the nervous system. Despite major advances in our understanding of the pathophysiology of mitochondrial diseases, clinical management of these conditions remains largely supportive. Using a systematic approach (Pfeffer et al., 2013, Nat, Rev. Neurol. (in press) PMID: 23817350), we identified 1,039 publications on treatments for mitochondrial diseases, only 35 of which included observations on more than five patients. Reports of a positive outcome on the basis of a biomarker of unproven clinical significance were more common in nonrandomized and nonblinded studies, suggesting a publication bias toward positive but poorly executed studies. Although trial design is improving, there is a critical need to develop new biomarkers of mitochondrial disease. A clinical trial is only as reliable as its outcomes, therefore the careful and systematic selection of outcome measures is extremely important. Currently, the selection of outcome measures for clinical trials designed to evaluate new drugs in patients with mitochondrial disorders is inefficient and has not been addressed systematically. Given that meaningful data can be obtained only from trials in which outcomes are assessed using valid instruments, one should first focus on the validation of a set of selected instruments in the target population. Using an extensive search of published literature, we systematically compiled a toolbox with outcome measures based on a primary search for possible instruments (Koene et al., 2013, Dev, Med. Child Neurol. 55:698-706). Subsequently, we reduced this toolbox using strict criteria that were adapted from the United States Food and Drug Administration. In coming years, more experience using these outcome measures in children with various mitochondrial disease phenotypes must be obtained before reliable conclusions regarding the validity of these instruments can be drawn.

Thus, in a preferred embodiment, the efficacy of treatment or suppressive therapy with the methods of the inventions can be determined using one or more of the outcome measures of the toolbox as listed in Table 1 of Koene et al (2013, supra), more preferably the efficacy is determined using one or more of the outcome measures of the "Common core set" in Table 1 of Koene et al (2013, supra).

In a further aspect the invention relates to a method of treating, preventing, or suppressing symptoms of a neoplastic disease, the method comprising administering to a subject an effective amount of one or more compounds of the invention as herein defined above. Alternatively, the invention relates to a compound of the invention as herein defined above, for use in a method of treating, preventing, or suppressing symptoms of a neoplastic. The methods of the invention, preferably comprise administering to a subject an effective amount of one or more compounds of the invention as herein defined above, and an acceptable carrier, excipient or vehicle, preferably a pharmaceutically or physiologically acceptable carrier, excipient or vehicle. Every cell, including neoplastic cells, needs energy. Shortage of energy therefore affects the activity of every cell and in principle every cell is affected by sub-optimally functioning mitochondria. However, the actual amount that is sub-optimal varies from cell to cell. Cells that have relatively high energy consumption such as rapidly dividing neoplastic cells typically require a higher amount of OXPHOS complexes than cells that have a low energy consumption, such as resting cells. Thus, neoplastic cells are more sensitive to down-regulation of mitochondrial function including OXPHOS than regular cells. Compounds of the invention having the effect of one or more of reduced of mitochondrial filamentation, induction of mitochondrial fragmentation, and reduced expression of OXPHOS enzymes, will therefore have a stronger effect on the activity and growth of neoplastic cells as compared to regular cells. As such the compounds having these effects may be used to reduce or inhibit growth of or even kill neoplastic cells.

In a preferred embodiment of the method of treating, preventing, or suppressing symptoms of a neoplastic disease, the neoplastic or proliferative disease is cancer. In particular embodiments, the cancer may be selected from the group comprising basal cell carcinoma, bone cancer, bowel cancer, brain cancer, breast cancer, cervical cancer, leukemia, liver cancer, lung cancer, lymphoma, melanoma, ovarian cancer, pancreatic cancer, prostate cancer or thyroid cancer. In other embodiments, the cancer may be selected from the group comprising acute lymphoblastic leukemia, acute myeloid leukemia, adrenocortical carcinoma, AIDS-related cancers, anal cancer, appendix cancer, astrocytoma, B-cell lymphoma, basal cell carcinoma, bile duct cancer, bladder cancer, bone cancer, bowel cancer, brainstem glioma, brain tumour, breast cancer, bronchial adenomas/carcinoids, Burkitt's lymphoma, carcinoid tumour, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumour, endometrial cancer, ependymoma, esophageal cancer, extracranial germ cell tumour, extragonadal germ cell tumour, extrahepatic bile duct cancer, eye cancer, intraocular melanoma/retinoblastoma, gallbladder cancer, gastric cancer, gastrointestinal carcinoid tumour, gastrointestinal stromal tumour (GIST), germ cell tumour, gestational trophoblastic tumour, glioma, gastric carcinoid, head and/or neck cancer, heart cancer, hepatocellular (liver) cancer, hypopharyngeal cancer, hypothalamic and visual pathway glioma, Kaposi sarcoma, kidney cancer, laryngeal cancer, leukemia (acute lymphoblastic/acute myeloid/chronic lymphocytic/chronic myelogenous/hairy cell), lip and/or oral cavity cancer, liver cancer, non-small cell lung cancer, small cell lung cancer, lymphoma (AIDS-related/Burkitt/cutaneous T-Cell/Hodgkin/non-Hodgkin/primary central nervous system), macroglobulinemia, malignant fibrous histiocytoma of bone/osteosarcoma, medulloblastoma, melanoma, Merkel cell carcinoma, mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, myelogenous leukemia, myeloid leukemia, myeloproliferative disorders, nasal cavity and/or paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumour, pancreatic cancer, islet cell cancer, paranasal sinus and nasal cavity cancer, parathyroid cancer, penile cancer, pharyngeal cancer, pheochromocytoma, pineal astrocytoma, pineal germinoma, pineoblastoma and/or supratentorial primitive neuroectodermal tumours, pituitary adenoma, plasma cell neoplasia/multiple myeloma, pleuropulmonary blastoma, primary central nervous system lymphoma, prostate cancer, rectal cancer, renal cell carcinoma, retinoblastoma, rhabdomyosarcoma, salivary gland cancer, Ewing sarcoma, Kaposi sarcoma, soft tissue sarcoma, uterine sarcoma, Sezary syndrome, skin cancer (non-melanoma), skin cancer (melanoma), skin carcinoma (Merkel cell), small cell lung cancer, small intestine cancer, soft tissue sarcoma, squamous cell carcinoma, squamous neck cancer with metastatic occult primary, stomach cancer, supratentorial primitive neuroectodermal tumour, T-cell lymphoma, testicular cancer, throat cancer, thymoma and/or thymic carcinoma, thyroid cancer, transitional cancer, trophoblastic tumour, ureter and/or renal pelvis cancer, urethral cancer, uterine endometrial cancer, uterine sarcoma, vaginal cancer, visual pathway and hypothalamic glioma, vulva cancer, Waldenstrom macroglobulinemia or Wilms tumour.

In yet another aspect the invention relates to the cosmetic use of the compounds of the invention. The compounds of the invention may thus be used (in methods) to revive the skin of a treated individual, particularly in individuals with aged skin, either due to aging or due to excessive exposure to sun.

Both conditions are related to the production of free radicals in skin. By at least one of induction of mitochondrial filamentation, prevention or reduction of mitochondrial fragmentation, and increased expression of OXPHOS enzymes in a cell of said individual it is possible to lower the action of free radicals in the skin and at least delay further aging in the skin. As such, one can also use a composition of the invention as a prophylactic, i.e. to at least reduce free radicals that would be capable to act on the skin, if left untreated. Thus preferably in this aspect of the invention compounds of the invention are applied the effect of which includes one or more of induction of mitochondrial filamentation, prevention or reduction of mitochondrial fragmentation, and increased expression of OXPHOS enzymes. Preferred compounds having these effects are indicated herein above.

The compounds of the invention can also be used in research applications, such as in vitro, in vivo, or ex vivo experiments in order to modulate one or more energy biomarkers in an experimental system. Such experimental systems can be cell samples, tissue samples, cell components or mixtures of cell components, partial organs, whole organs, or organisms. Such research applications can include, but are not limited to, use as assay reagents, elucidation of biochemical pathways, or evaluation of the effects of other agents on the metabolic state of the experimental system in the presence/absence of one or more compounds of the invention.

Additionally, the compounds of the invention can be used in biochemical tests or assays. Such tests can include incubation of one or more compounds of the invention with a tissue or cell sample from a subject to evaluate a subject's potential response (or the response of a specific subset of subjects) to administration of said one or more compounds, or to determine which compound of the invention produces the optimum effect in a specific subject or subset of subjects. One such test or assay would involve 1) obtaining a cell sample or tissue sample from a subject or set of subjects in which modulation of one or more energy biomarkers can be assayed; 2) administering one or more compounds of the invention to the cell sample(s) or tissue sample(s); and 3) determining the amount of modulation of the one or more energy biomarkers after administration of the one or more compounds, compared to the status of the energy biomarker prior to administration of the one or more compounds.

Another such test or assay would involve 1) obtaining a cell sample or tissue sample from a subject or set of subjects in which modulation of one or more energy biomarkers can be assayed; 2) administering at least two compounds of the invention to the cell sample(s) or tissue sample(s); 3) determining the amount of modulation of the one or more energy biomarkers after administration of the at least two compounds, compared to the status of the energy biomarker prior to administration of the at least two compounds, and 4) selecting a compound for use in treatment, suppression, or modulation based on the amount of modulation determined in step 3).

The compositions comprising the compounds of the invention, as described above, can be prepared as a medicinal or cosmetic preparation or in various other media, such as foods for humans or animals, including medical foods and dietary supplements. A "medical food" is a product that is intended for the specific dietary management of a disease or condition for which distinctive nutritional requirements exist. By way of example, but not limitation, medical foods may include vitamin and mineral formulations fed through a feeding tube (referred to as enteral administration). A "dietary supplement" shall mean a product that is intended to supplement the human diet and is typically provided in the form of a pill, capsule, and tablet or like formulation. By way of example, but not limitation, a dietary supplement may include one or more of the following ingredients: vitamins, minerals, herbs, botanicals; amino acids, dietary substances intended to supplement the diet by increasing total dietary intake, and concentrates, metabolites, constituents, extracts or combinations of any of the foregoing. Dietary supplements may also be incorporated into food, including, but not limited to, food bars, beverages, powders, cereals, cooked foods, food additives and candies; or other functional foods designed to promote cerebral health or to prevent or halt the progression of a neurodegenerative disease involving mitochondrial dysfunction. If administered as a medicinal preparation, the composition can be administered, either as a prophylaxis or treatment, to a patient in any of a number of methods. The compositions may be administered alone or in combination with other pharmaceutical or cosmetic agents and can be combined with a physiologically acceptable carrier thereof. The effective amount and method of administration of the particular formulation can vary based on the individual subject, the condition or the stage of disease, and other factors evident to one skilled in the art. During the course of the treatment, the concentration of the subject compositions may be monitored to insure that the desired level is maintained. The subject compositions may be compounded with other physiologically acceptable materials which can be ingested including, but not limited to, foods.

The compounds described herein can be formulated as pharmaceutical or cosmetic compositions by formulation with additives such as pharmaceutically or physiologically acceptable excipients carriers, and vehicles. Suitable pharmaceutically or physiologically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-P-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21" edition (2005), incorporated herein by reference.

A pharmaceutical or cosmetic composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical or cosmetic compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e. g. as mists or sprays), rectally, or topically in dosage unit formulations containing conventional nontoxic pharmaceutically or physiologically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e. g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N. Y., p. 33 et seq (1976).

The invention also provides articles of manufacture and kits containing materials useful for treating, preventing, or suppressing symptoms associated with a mitochondrial disorder or with a condition associated with mitochondrial dysfunction. The article of manufacture comprises a container with a label. Suitable containers include, for example, bottles, vials, and test tubes. The containers may be formed from a variety of materials such as glass or plastic. The container holds a composition having an active agent which is effective for treating, preventing, or suppressing symptoms associated with a mitochondrial disorder or with a condition associated with mitochondrial dysfunction. The active agent in the composition is one or more of the compounds of the invention. The label on the container preferably indicates that the composition is used for treating, preventing, or suppressing symptoms associated with a mitochondrial disorder or with a condition associated with mitochondrial dysfunction, and may also indicate directions for either in vivo or in vitro use, such as those described above.

The invention also provides kits comprising any one or more of the compounds of the invention. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, methods for treating, preventing, or suppressing symptoms associated with a mitochondrial disorder or with a condition associated with mitochondrial dysfunction.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy or condition to be treated. The unit dosage chosen is usually fabricated and administered to provide a defined final concentration of drug in the blood, tissues, organs, or other targeted region of the body. The effective amount for a given situation can be readily determined by routine experimentation and is within the skill and judgment of the ordinary clinician or skilled person.

Examples of dosages which can be used are an effective amount of the compounds of the invention within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds of the present invention may be administered in a single daily dose, or the total daily dosage may be administered in divided dosage of two, three or four times daily.

While the compounds of the invention can be administered as the sole active pharmaceutical or cosmetic agent, they can also be used in combination with one or more other agents used in the treatment or suppression of disorders. Representative agents useful in combination with the compounds of the invention for the treating, preventing, or suppressing symptoms associated with a mitochondrial disorder or with a condition associated with mitochondrial dysfunction include, but are not limited to, Coenzyme Q, vitamin E, idebenone, MitoQ, EPI-743, vitamin K and analogues thereof, naphtoquinones and derivatives thereof, other vitamins, and antioxidant compounds. When additional active agents are used in combination with the compounds of the present invention, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIG. 1a), compound K (KH002; FIG. 1b) or compound N (KH003; FIG. 1c) at the indicated concentrations. CT is the control human skin fibroblast cell line 5120-C, P1 is the patient cell line 7206-S7, P2 is the patient cell line 5175-S7, C I is the fully assembled protein complex I, and C II is the fully assembled protein complex II.

FIG. 3a), compound K (KH002; FIG. 3b) or compound N (KH003; FIG. 3c). After 72 hours, the formation of CM-DCF was measured as an indirect indication of the intracellular ROS levels. N indicates the number of independent experiments, n indicates the number of samples within each experiment, and veh (vehicle is set as 100%) indicates that the cell line is treated with 0.1% DMSO only.

LIST OF ABBREVIATIONS

Figure 1A:
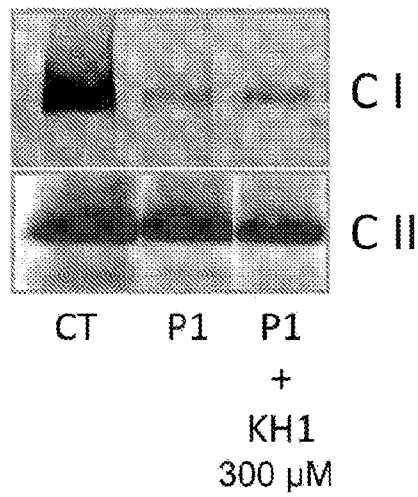
FIGS. 1a-1c. The protein expression levels of complex I and II as determined by western blotting after exposure of the cells for 72 hours to compound F (KH001.

8-OHdG 8-hydroxy-2'-deoxyguanosine
Ac acetate
ACBT ε-aminocaproic acid and BisTris/HCl
ADP adenosine diphosphate
AKBR acetoacetate/3-hydroxybutyrate
ALS amyotrophic lateral sclerosis
AT anaerobic threshold
ATP adenosine triphosphate
Boc tert-butoxycarbonyl
BMI body mass index
BMR basal metabolic rate
BN-PAGE Blue Native polyacrylamide gel electrophoresis
CM-$H_2$DCFDA 5-(and-6)-chloromethyl-2',7'-dichlorodihydrofluorescein diacetate
CO cardiac output
CPEO Chronic Progressive External Ophtalmoplegia
CSA cyclosporin A
CT control human primary skin fibroblast cell line
CYT C cytochrome c
DCM dichloromethane
DIPEA N,N-diisopropylethylamine
DMF dimethylformamide
DMSO dimethyl sulfoxide
DOA dominant optic atrophy
EDCI 1-ethyl-3-(3-dimethylaminopropyl)carbodiimide
EDTA ethylenediaminetetraacetic acid
Et ethyl
FRDA Friedreich's ataxia
Gly glycyl
HEPES 4-(2-hydroxyethyl)-1-piperazineethanesulfonic acid
HOBt hydroxybenzotriazole
HPLC high-performance liquid chromatography
HR heart rate
ITIES interfaces between two immiscible electrolyte solutions
KSS Kearns-Sayre Syndrome
LHON Leber's Hereditary Optic Neuropathy
Me methyl
MEGDEL 3-methylglutaconic aciduria, sensorineural deafness, encephalopathy and neuro-radiological findings of Leigh-like syndrome
MELAS mitochondrial myopathy, encephalopathy, lactacidosis, and stroke
MERRF Myoclonus Epilepsy Associated with Ragged-Red Fibers
MIDD Maternally Inherited Diabetes and Deafness
Mito$Q_{10}$ mitoquinone
MNGIE Mitochondrial Neuro-Gastro-Intestinal Encephalopathy
MRS magnetic resonance spectroscopy
$NAD^+$ nicotinamide adenine dinucleotide
NADH reduced nicotinamide adenine dinucleotide
NARP neuropathy, ataxia and retinitis pigmentosa
NMM N-methylmorpholine
Orn ornithyl
OXPHOS oxidative phosphorylation
PBS phosphate-buffered saline
PCr phosphocreatine
PDR Physicians' Desk Reference
PVDF polyvinylidene difluoride
Qc cardiac output
QSPR Quantitative Structure-Property Relationship
ROS reactive oxygen species
RQ respiratory quotient
Su succinimide
THF tetrahydrofuran
TFA trifluoroacetate
TFAH trifluoroacetic acid
VCO2 levels of carbon dioxide output
VO2 levels of oxygen consumption
VO2max whole body oxygen consumption
Z benzyloxycarbonyl

EXAMPLES

Example 1

Synthesis of Compounds 1.1 Synthesis of Compounds F, K, N and O
1.1.1 General Information Unless noted otherwise, materials were purchased from commercial suppliers and used as received. $CH_2Cl_2$ was freshly distilled from calcium hydride. All air and moisture sensitive reactions were carried out under an inert atmosphere of dry nitrogen. Column chromatography was performed using Acros silica gel (0.035-0.070 mm, 6 nm).

1.1.2 Synthesis of Trolox™ 2-guanidinoglycylaminoethylamide trifluoroacetate (Compound F)

STEP A: To a solution of Trolox™ (1.2 g, 4.65 mmol) in DMF (45 mL) was added HOBt (0.691 g, 5.12 mmol), followed by EDCI (0.981 g, 5.12 mmol). The mixture was stirred until a clear solution was obtained. Next, DIPEA (0.891 mL, 5.12 mmol) was added dropwise. The solution was cooled to 4° C. (ice bath) and Boc-ethylenediamine (0.811 mL, 4.88 mmol) was added. The mixture was stirred at 4° C. for 5 min, allowed to warm to room temperature and stirred for an additional 1 h. The mixture was then diluted with EtOAc (200 mL) and washed with aqueous citric acid (10 wt %, 2×60 mL). The combined aqueous phases were extracted with EtOAc (60 mL), after which the organic phases were combined and washed with $H_2O$ (60 mL), sat. aq. $NaHCO_3$ (60 mL), $H_2O$ (60 mL) and brine (60 mL), dried over $Na_2SO_4$, filtered and concentrated in vacuo. The obtained INTERMEDIATE A (1.8 g) was used in the next step without further purification.

STEP B: To a solution of INTERMEDIATE A (1.75 g, 4.46 mmol) in EtOAc (25 mL) was added a freshly prepared saturated solution of HCl in EtOAc (45 mL). The solution was stirred for 45 min, during which a white precipitate was formed. The suspension was then diluted with $Et_2O$ (150 mL) and the resulting mixture was stirred for an additional 30 min. The solids were collected by filtration, washed with $Et_2O$ (2×30 mL) and dried in vacuo. The obtained INTERMEDIATE B (1.36 g) was used in the next step without further purification.

STEP C: A solution of INTERMEDIATE B (1.32 g, 4.0 mmol) in DMF (40 mL) was cooled to 4° C. (ice bath). Next, DIPEA (1.5 mL, 8.8 mmol) was added dropwise, followed by portionwise addition of Boc-Gly-OSu (1.1 g, 4.0 mmol). The mixture was allowed to warm to room temperature and stirred for 1.5 h. Then, the mixture was diluted with EtOAc (250 mL) and washed with aqueous citric acid (10 wt %, 2×50 mL), $H_2O$ (50 mL), sat. aq. $NaHCO_3$ (2×50 mL), $H_2O$ (50 mL) and brine (50 mL), dried over $Na_2SO_4$, filtered and concentrated in vacuo. The obtained INTERMEDIATE C (1.52 g) was used in the next step without further purification.

STEP D: To a solution of INTERMEDIATE C (1.42 g, 3.16 mmol) in EtOAc (20 mL) was added a freshly prepared saturated solution of HCl in EtOAc (40 mL). The solution was stirred for 1 h, during which a white precipitate was formed. The suspension was then diluted with Et$_2$O (120 mL) and the resulting mixture was stirred for an additional 30 min. The solids were collected by filtration, washed with Et$_2$O (2×25 mL) and dried in vacuo. The obtained INTERMEDIATE D (925 mg) was used in the next step without further purification.

STEP E: To a solution of INTERMEDIATE D (200 mg, 0.52 mmol) in DMF (3 mL) was added NMM (0.15 mL, 1.35 mmol), followed by 1,3-di-Boc-2-(trifluoromethylsulfonyl) guanidine (223 mg, 0.57 mmol). The resulting mixture was stirred for 16 h. Next, the mixture was diluted with EtOAc (15 mL), extracted with aqueous citric acid (10 wt %, 2×5 mL), H$_2$O (5 mL), brine (2×5 mL), dried over Na$_2$SO$_4$, filtered and concentrated in vacuo. Purification by flash column chromatography (EtOAc/heptane 2:1) afforded INTERMEDIATE E (259 mg) as a white solid.

STEP F: A solution of INTERMEDIATE E (144 mg, 0.24 mmol) in TFA/DCM (1:1 v/v, 4 mL) was stirred for 2 h. The solution was then diluted with toluene (2×10 mL) and concentrated in vacuo. The residue was stripped with H$_2$O (2×10 mL) and lyophilized from H$_2$O (3 mL), affording Trolox™ 2-guanidinoglycylamino-ethylamide trifluoroacetate (123 mg) as a white powder.

$^1$H NMR of compound F (D$_2$O, 400 MHz): δ (ppm)=3.74 (s, 2H), 3.44-3.21 (m, 4H), 2.72-2.60 (m, 1H), 2.54-2.41 (m, 1H), 2.35-2.25 (m, 1H), 2.17 (s, 3H), 2.16 (s, 3H), 2.07 (s, 3H), 1.88-1.77 (m, 1H), 1.50 (s, 3H).

1.1.3 Trolox™ 2-acetamidinoglycylaminoethylamide hydrochloride (Compound K)

STEP G: To a solution of INTERMEDIATED (136 mg, 0.35 mmol) in methanol (4 mL), was added NH$_3$ in methanol (7N, 0.2 mL), followed by portionwise addition of ethyl acetimidate hydrochloride (65 mg, 0.53 mmol). The mixture was stirred for 15 min. Next, silica gel (400 mg) was added to the solution and the resulting mixture was concentrated under reduced. Purification by flash column chromatography (DCM/methanol 9:1 to 8:2), followed by lyophilization from H$_2$O (3 mL) afforded Trolox™ 2-acetamidinoglycylaminoethylamide hydrochloride (120 mg) as off-white powder.

$^1$H NMR of compound K (D$_2$O, 400 MHz): δ (ppm)=3.86-3.75 (m, 2H), 3.46-3.23 (m, 4H), 2.72-2.63 (m, 1H), 2.51-2.47 (m, 1H), 2.35-2.28 (m, 1H), 2.29 (s, 3H), 2.18 (s, 3H), 2.16 (s, 3H), 2.07 (s, 3H), 1.87-1.78 (m, 1H), 1.51 (s, 3H).

1.1.4 Trolox™ Ornithylamide Hydrochloride (Compound N)

STEP H: A solution of Z-Orn(Boc)-OH (2.5 g, 6.8 mmol) in DMF (7 mL) was cooled to 4° C. (ice bath), after which potassium carbonate (0.94 g, 6.8 mmol) was added portionwise. The resulting suspension was allowed to stir for 5 min, after which iodomethane (0.51 mL, 8.2 mmol) was added dropwise. The mixture was allowed to warm to room temperature and stirred for 2.5 h. Next, H$_2$O (10 mL) was added and the aqueous phase was extracted with EtOAc (3×10 mL). The combined organic layers were washed with aqueous Na$_2$S$_2$O$_5$ (2.5 wt %, 5 mL) and brine (5 mL), dried over Na$_2$SO$_4$, filtered and concentrated in vacuo. The obtained INTERMEDIATE H (2.43 g) was used in the next step without further purification.

STEP I: To a solution of INTERMEDIATE H (2.4 g, 6.4 mmol) in iso-propanol (54 mL) was added dropwise acetic acid (0.4 mL, 7 mmol), followed by a suspension of palladium on carbon (10 wt %, 0.68 g, 0.64 mmol) in H$_2$O (6 mL). The resulting black suspension was placed under an atmosphere of H$_2$ and stirred for 3 h. Next, the reaction mixture was purged with nitrogen gas for 5 min, after which the mixture was filtered through Celite. The filtrate was concentrated in vacuo, affording INTERMEDIATE I (1.76 g) as a colorless oil which was used in the next step without further purification.

STEP J: To a solution of Trolox™ (0.72 g, 2.8 mmol) in DMF (22 mL) was added HOBt (0.42 g, 3.1 mmol), followed by EDCI (0.59 g, 3.1 mmol). The mixture was stirred until a clear solution was obtained. Next, DIPEA (0.54 mL, 3.1 mmol) was added dropwise. The solution was cooled to 4° C. (ice bath) and INTERMEDIATE I (900 mg, 2.94 mmol) was added. The mixture was stirred at 4° C. for 5 min, allowed to warm to room temperature and stirred for an additional 1 h. The mixture was then diluted with EtOAc (120 mL) and washed with aqueous citric acid (10 wt %, 2×40 mL). The combined aqueous phases were extracted with EtOAc (40 mL), after which the organic phases were combined and washed with H$_2$O (40 mL), sat. aq. NaHCO$_3$ (40 mL), H$_2$O (40 mL) and brine (40 mL), dried over Na$_2$SO$_4$, filtered and concentrated in vacuo. Purification by flash column chromatography (EtOAc/heptane 1:1) afforded INTERMEDIATE J (1.1 g) as a white foam.

STEP K: A solution of INTERMEDIATE J (587 mg, 1.23 mmol) in THF (2.5 mL) was cooled to 4° C. (ice bath). Next, aqueous NaOH (1M, 2.5 mL, 2.5 mmol) was added dropwise. The solution was allowed to warm to room temperature and the mixture was stirred for 1 h. Then, the mixture was diluted with H$_2$O (15 mL) and Et$_2$O (15 mL). The layers were mixed and then separated. The aqueous phase was washed with Et$_2$O (15 mL), acidified to pH=2.5 using sat. aq. KHSO$_4$, and extracted with Et$_2$O (2×10 mL). The last two organic phases were combined, washed with sat. aq. NH$_4$Cl (2×10 mL), brine (10 mL), dried over Na$_2$SO$_4$, filtered and concentrated in vacuo. The obtained INTERMEDIATE K (490 mg) was used in the next step without further purification.

STEP L: A solution of INTERMEDIATE K (170 mg, 0.36 mmol) in EtOAc (4 mL) was purged with HCl (g) for 25 min. Next, the solution was purged with argon for 15 min, which resulted in the formation of a precipitate. The mixture was diluted with Et$_2$O (20 mL), stirred for 15 min after which the formed solids were collected by filtration. The solids were lyophilized from H$_2$O (3 mL), affording Trolox™ ornithylamide hydrochloride (115 mg) as an off-white solid.

$^1$H NMR of compound N (1:1 mixture of diastereomers, D$_2$O, 400 MHz): δ (ppm)=4.38-4.23 (m, 2×1H), 3.01-2.93 (m, 2H), 2.73-2.27 (m, 2H+2×3H), 2.21 (s, 3H), 2.19 (s, 3H), 2.15 (s, 2×3H), 2.05 (s, 2×3H), 2.00-1.73 (m, 2×3H), 1.68-1.51 (m, 2×1H), 1.58 (s, 3H), 1.55 (s, 3H), 1.12-0.94 (m, 2×1H). 1.1.5 Trolox™ Arginylamide Hydrochloride (Compound O)

STEP M: To a solution of Trolox™ (0.49 g, 1.9 mmol) in DMF (20 mL) was added HOBt (0.29 g, 2.1 mmol), followed by EDCI (0.40 g, 2.1 mmol). The mixture was stirred until a clear solution was obtained. Next, DIPEA (0.37 mL, 2.1 mmol) was added dropwise. The solution was cooled to 4° C. (ice bath) and a H-Arg(PMC)-OtBu (1.0 g, 2.0 mmol) was added. The mixture was stirred at 4° C. for 5 min, allowed to warm to room temperature and stirred for an additional 1 h.

The mixture was then diluted with EtOAc (100 mL) and washed with aqueous citric acid (10 wt %, 2×30 mL). The combined aqueous phases were extracted with EtOAc (30 mL), after which the organic phases were combined and washed with $H_2O$ (30 mL), sat. aq. $NaHCO_3$ (30 mL), $H_2O$ (30 mL) and brine (30 mL), dried over $Na_2SO_4$, filtered and concentrated in vacuo. The obtained INTERMEDIATE M (1.31 g) was used in the next step without further purification.

STEP N: A solution of INTERMEDIATE M (200 mg, 0.27 mmol) in DCM/TFA (1:1 v/v, 3 mL) was stirred for 30 min. Next, the mixture was diluted with toluene (10 mL) and concentrated under reduced pressure. The residue was stripped with toluene (2×10 mL) and taken up in water (10 mL). The resulting suspension was acidified using aqueous HCl (1M, 55 mL), diluted with $Et_2O$ (10 mL) and stirred vigorously for 15 min. The layers were separated and the aqueous phase was washed with $Et_2O$ (2×10 mL). Lyophilization of the aqueous phase afforded Trolox™ arginylamide hydrochloride (120 mg) as an off-white solid.

$^1$H NMR of compound O (1:1 mixture of diastereomers, $D_2O$, 400 MHz): δ (ppm)=4.35 (dd, J=8.6, 4.0 Hz, 1H), 4.24 (dd, J=8.6, 4.8 Hz, 1H), 3.08 (t, J=7.2 Hz, 2H), 2.76 (t, J=7.4 Hz, 2H), 2.59-2.33 (m, 2×3H), 2.23 (s, 3H), 2.21 (s, 3H), 2.16 (s, 2×3H), 2.07 (s, 3H), 2.06 (s, 3H), 1.98-1.73 (m, 2×3H), 1.62 (s, 3H), 1.57 (s, 3H), 1.57-1.30 (m, 2×1H), 1.00-0.76 (m, 2×1H).

1.2 Synthesis of Compounds R-T, S-T, R-U, S-U, R-V, S-V R,R-X, R,S-X, S,R-X, S,S-X, Rac-Z, R,Trans-AE, S,Trans-AE, S,R-AF, S,R-AG, S,S-AG and S-AH

1.2.1 General Information

GENERAL PROCEDURE A for the EDCI/HOAt coupling of amines to Trolox™: To a mixture of Trolox™ (1 eq) and amine (1 eq) in DMF (dry, 0.2M) under nitrogen atmosphere were added EDCl.HCl (1.1 eq) and HOAt (0.1 eq). The mixture was stirred at room temperature until complete conversion (LCMS). The mixture was diluted with $H_2O$ (20 mL) and extracted with EtOAc (3×20 mL). The combined organic phases were successively washed with 0.5M $KHSO_4$ (20 mL), sat. aq. $NaHCO_3$ (20 mL) and brine (3×20 mL). The organic phase was dried over $Na_2SO_4$, filtered and concentrated in vacuo.

GENERAL PROCEDURE B for BOC-deprotection: To a solution of INTERMEDIATE A (1 eq) in DCM (~0.03M) was added 4N HCl in dioxane (36 eq). The mixture was stirred at room temperature until complete conversion (LCMS), concentrated, coevaporated with DCM (2×), purified by reversed phase column chromatography ($H_2O$+0.01% (w/w) formic acid/MeCN) and freeze-dried.

1.2.2 Trolox™ Piperidin-3-Amide Hydrochloride (Compound X, R,R-Stereoisomer)

STEP A: According to general procedure A INTERMEDIATE Xa was prepared, using (R)-Trolox™ (250 mg) and (R)-3-amino-1-N-Boc-piperidine (200 mg). INTERMEDIATE Xa (349 mg) was used in the next step without further purification.

STEP B: According to general procedure B FINAL COMPOUND R,R-X (209 mg) was prepared. $^1$H NMR (400 MHz, DMSO): δ (ppm): 8.23 (1H, s), 7.55 (1H, br s), 7.30 (1H, d, J=8.4 Hz), 3.85-3.73 (1H, m), 2.99-2.90 (1H, m), 2.89-2.79 (1H, m), 2.73-2.64 (1H, m), 2.64-2.37 (3H, m), 2.23-2.14 (1H, m), 2.11 (3H, s), 2.07 (3H, s), 1.99 (3H, s), 1.79-1.67 (1H, m), 1.54-1.45 (1H, m), 1.44-1.26 (3H, m), 1.39 (3H, s).

1.2.3 Trolox™ piperidin-3-amide hydrochloride (Compound X, R,S-Stereoisomer)

STEP A: According to general procedure A INTERMEDIATE Xb was prepared, using (R)-Trolox™ (100 mg) and (S)-3-amino-1-N-Boc-piperidine (80 mg). INTERMEDIATE Xb (143 mg) was used in the next step without further purification.

STEP B: According to general procedure B FINAL COMPOUND R,S-X (68 mg) was prepared. $^1$H NMR (400 MHz, DMSO): δ (ppm): 8.25 (1H, s), 7.53 (1H, br s), 7.26 (1H, d, J=8.4 Hz), 3.78-3.64 (1H, m), 2.83-2.71 (2H, m), 2.63-2.34 (4H, m), 2.17-2.03 (1H, m), 2.09 (3H, s), 2.07 (3H, s), 1.99 (3H, s), 1.82-1.72 (1H, m), 1.72-1.55 (2H, m), 1.54-1.41 (2H, m), 1.36 (3H, s).

1.2.4 Trolox™ 4-Diemthylaminobutylamide Hydrochloride (Compound V, R-Stereoisomer)

According to general procedure A FINAL COMPOUND R-V was prepared, using (R)-Trolox™ (100 mg) and 4-(Dimethylamino)butylamine (46 mg). When the reaction reached complete conversion, the mixture was quenched with $H_2O$ (20 mL), basified with sat. aq. $Na_2CO_3$ until pH ~9 and extracted with EtOAc (3×40 mL). The combined organic phases were dried over $Na_2SO_4$, filtered and concentrated in vacuo. The crude material was purified by silica column chromatography (DCM/7N $NH_3$ in MeOH), dissolved in diethyl ether (5 mL) and treated with 1N HCl in diethyl ether (1 mL). The mixture was concentrated in vacuo, coevaporated with DCM (3×) and freeze-dried ($H_2O$/MeCN) to obtain FINAL COMPOUND R-V (86 mg). $^1$H NMR (400 MHz, DMSO): δ (ppm): 10.14 (1H, s), 7.53 (1H, br s), 7.46-7.38 (1H, m), 3.17-2.99 (2H, m), 2.98-2.87 (2H, m), 2.63 (6H, s), 2.57-2.35 (2H, m), 2.22-2.13 (1H, m), 2.10 (3H, s), 2.07 (3H, s), 1.99 (3H, s), 1.78-1.65 (1H, m), 1.50-1.29 (4H, m), 1.37 (3H, s).

1.2.5 Trolox™ 4-Diemthylaminobutylamide Hydrochloride (Compound V, S-Stereoisomer)

According to general procedure A FINAL COMPOUND S-V was prepared, using (S)-Trolox™ (100 mg) and 4-(Dimethylamino)butylamine (46 mg). When the reaction reached complete conversion, the mixture was quenched with $H_2O$ (20 mL), basified with sat. aq. $Na_2CO_3$ until pH ~9 and extracted with EtOAc (3×40 mL). The combined organic phases were dried over $Na_2SO_4$, filtered and concentrated in vacuo. The crude material was purified by silica column chromatography (DCM/7N $NH_3$ in MeOH), dissolved in diethyl ether (5 mL) and treated with 1N HCl in diethyl ether (1 mL). The mixture was concentrated in vacuo, coevaporated with DCM (3×) and freeze-dried ($H_2O$/MeCN) to obtain FINAL COMPOUND S-V (92 mg). $^1$H NMR (400 MHz, DMSO): δ (ppm): 10.12 (1H, s), 7.53 (1H, br s), 7.42 (1H, t, J=5.92 Hz), 3.16-2.99 (2H, m), 2.98-2.86 (2H, m), 2.63 (6H, s), 2.58-2.35 (2H, m), 2.23-2.14 (1H, m), 2.11 (3H, s), 2.07 (3H, s), 1.99 (3H, s), 1.78-1.64 (1H, m), 1.53-1.29 (4H, m), 1.37 (3H, s).

1.2.6 Trolox™ Piperidin-3-Amide Hydrochloride (Compound X, S,R-Stereoisomer)

STEP A: According to general procedure A INTERMEDIATE Xc was prepared, using (S)-Trolox™ (5.49 g) and (R)-

3-amino-1-N-Boc-piperidine (4.39 g). After purification by silica column chromatography (Heptane/EtOAc) INTERMEDIATE Xc (6.11 g) was used in the next step.

STEP B: According to general procedure B, without purification by reversed phase column chromatography, FINAL COMPOUND S,R-X (4.43 g) was prepared. 1H NMR (400 MHz, DMSO): δ (ppm): 8.95 (2H, s), 7.58-7.48 (2H, m), 4.03-3.88 (1H, m), 3.16-3.05 (1H, m), 3.03-2.93 (1H, m), 2.76-2.62 (2H, m), 2.60-2.37 (2H, m), 2.18-2.03 (1H, m), 2.08 (3H, s), 2.07 (3H, s), 2.00 (3H, s), 1.86-1.72 (3H, m), 1.72-1.45 (2H, m), 1.36 (3H, s).

1.2.7 Trolox™ piperidin-3-amide hydrochloride (Compound X, S,S-Stereoisomer)

STEP A: According to general procedure A INTERMEDIATE Xd was prepared, using (S)-Trolox™ (100 mg) and (S)-3-amino-1-N-Boc-piperidine (80 mg). INTERMEDIATE Xd (158 mg) was used in the next step without further purification.

STEP B: According to general procedure B FINAL COMPOUND S,S-X (122 mg) was prepared. $^1$H NMR (400 MHz, DMSO): δ (ppm): 8.24 (1H, s), 7.56 (1H, br s), 7.28 (1H, d, J=8.4 Hz), 3.82-3.69 (1H, m), 2.95-2.85 (1H, m), 2.85-2.73 (1H, m), 2.70-2.61 (1H, m), 2.61-2.35 (3H, m), 2.23-2.13 (1H, m), 2.11 (3H, s), 2.07 (3H, s), 1.99 (3H, s), 1.79-1.66 (1H, m), 1.53-1.42 (1H, m), 1.42-1.24 (3H, m), 1.39 (3H, s).

1.2.8 Trolox™ 1-methylpiperidinium-4-amide formate (Compound AH, S-Stereoisomer)

To a mixture of (S)-Trolox™ (100 mg) and 1-methylpiperidin-4-amine (46 mg) in DMF (dry, 2 ml) was added PyBOP (249 mg, 1.2 eq). After stirring for one night at room temperature the mixture was quenched with H$_2$O (20 ml). sat. aq. NaHCO$_3$ (30 ml) was added and the aqueous phase was extracted with EtOAc (3×30 ml). The combined organic phases were dried over Na$_2$SO$_4$, filtered and concentrated in vacuo. The crude material was purified by reversed phase column chromatography ((H$_2$O+0.01% (w/w) formic acid/MeCN) and freeze-dried to obtain FINAL COMPOUND S-AH (75 mg). $^1$H NMR (400 MHz, DMSO): δ (ppm): 8.21 (1H, s), 7.57 (1H, br s), 6.91 (1H, d, J=7.32 Hz), 3.64-3.43 (1H, m), 2.62-2.27 (4H, m), 2.24-2.01 (3H, m), 2.14 (3H, s), 2.10 (3H, s), 2.07 (3H, s), 1.98 (3H, s), 1.78-1.62 (2H, m), 1.57-1.42 (2H, m), 1.42-1.29 (1H, m), 1.38 (3H, s).

1.2.9 Trolox™ 4-aminocyclohexylamide hydrochloride (Compound AE, R,Trans-Stereoisomer)

STEP A: According to general procedure A INTERMEDIATE AEa was prepared, using (R)-Trolox™ (100 mg) and N-Boc-trans-1,4-cyclohexanediamine (86 mg). INTERMEDIATE AEa (186 mg) was used in the next step without further purification.

STEP B: According to general procedure B FINAL COMPOUND R,trans-AE (102 mg) was prepared. $^1$H NMR (400 MHz, DMSO): δ (ppm): 8.42 (1H, s), 7.57 (2H, br s), 6.92 (1H, d, J=8.3 Hz), 3.79-2.98 (1H, m), 2.84-2.69 (1H, m), 2.61-2.36 (2H, m), 2.19-1.91 (1H, m), 2.07 (3H, s), 2.06 (3H, s), 1.99 (3H, s), 1.89-1.65 (4H, m), 1.61-1.46 (1H, m), 1.40-1.05 (4H, m), 1.35 (3H, s).

1.2.10 Trolox™ 4-aminocyclohexylamide hydrochloride (Compound AE, S,Trans-Stereoisomer)

STEP A: According to general procedure A INTERMEDIATE AEb was prepared, using (S)-Trolox™ (100 mg) and N-Boc-trans-1,4-cyclohexanediamine (86 mg). INTERMEDIATE AEb (182 mg) was used in the next step without further purification.

STEP B: According to general procedure B FINAL COMPOUND S,trans-AE (84 mg) was prepared. 1H NMR (400 MHz, DMSO): δ (ppm): 8.43 (1H, s), 7.57 (2H, br s), 6.93 (1H, d, J=8.4 Hz), 3.53-3.35 (1H, m), 2.86-2.72 (1H, m), 2.60-2.36 (2H, m), 2.21-1.92 (1H, m), 2.08 (3H, s), 2.07 (3H, s), 1.98 (3H, s), 1.90-1.66 (4H, m), 1.61-1.47 (1H, m), 1.41-1.08 (4H, m), 1.35 (3H, s).

1.2.11 Trolox™ 4-aminobutylamide hydrochloride (Compound T, R-Stereoisomer)

STEP A: INTERMEDIATE Ta was prepared, using (R)-Trolox™ (200 mg) and N-Boc-1,4-butanediamine (150 mg). To a cooled (0° C.) mixture of the reactants in DMF (dry, 0.05 M) under nitrogen atmosphere were added EDCI.HCl (1.1 eq) and HOAt (0.1 eq). The mixture was stirred 1 hour at 0° C. and was allowed to reach room temperature and stirred until complete conversion (LCMS). The reaction mixture was poured into 10 eq (to DMF) of water and extracted with EtOAc (3×50 mL). The combined organic phases were successively washed with 0.5M KHSO$_4$ (50 mL), sat. aq. NaHCO3 (50 mL) and brine (3×50 mL). The organic phase was dried over Na$_2$SO$_4$, filtered and concentrated in vacuo. INTERMEDIATE Ta (100 mg) was used in the next step without further purification.

Step B: According to general procedure B FINAL COMPOUND R-T (66 mg) was prepared. $^1$H NMR (400 MHz, DMSO): δ (ppm): 8.41 (1H, s), 7.34 (2H, t, J=6.0 Hz), 3.14-2.95 (2H, m), 2.72-2.59 (2H, m), 2.54 (1H, s), 2.47-2.34 (2H, m), 2.21-2.12 (1H, m), 2.09 (3H, s), 2.07 (3H, s), 1.99 (3H, s), 1.79-1.65 (1H, m), 1.45-1.27 (4H, m), 1.35 (3H, s).

1.2.12 Trolox™ 4-Aminobutylamide Hydrochloride (Compound T, S-Stereoisomer)

Step A: INTERMEDIATE Tb was prepared, using (S)-Trolox™ (200 mg) and N-Boc-1,4-butanediamine (150 mg). To a cooled (0° C.) mixture of the reactants in DMF (dry, 0.05 M) under nitrogen atmosphere were added EDCI.HCl (1.1 eq) and HOAt (0.1 eq). The mixture was stirred 1 hour at 0° C. and was allowed to reach room temperature and stirred until complete conversion (LCMS). The reaction mixture was poured into 10 eq (to DMF) of water and extracted with EtOAc (3×50 mL). The combined organic phases were successively washed with 0.5M KHSO$_4$ (50 mL), sat. aq. NaHCO3 (50 mL) and brine (3×50 mL). The organic phase was dried over Na2SO4, filtered and concentrated in vacuo. INTERMEDIATE Tb (100 mg) was used in the next step without further purification.

Step B: According to general procedure B FINAL COMPOUND S-T (67 mg) was prepared. 1H NMR (400 MHz, DMSO): δ (ppm): 8.41 (1H, s), 7.37-7.30 (1H, m), 3.13-2.97 (3H, m), 2.68-2.61 (2H, m), 2.20-2.11 (1H, m), 2.09 (3H, s), 2.07 (3H, s), 1.99 (3H, s), 1.79-1.66 (1H, m), 1.46-1.23 (4H, m), 1.35 (3H, s).

1.2.13 Trolox™ 5-aminopentylamidehydrochloride (Compound U, R-Stereoisomer)

Step A: INTERMEDIATE Ua was prepared, using (R)-Trolox™ (200 mg) and 1-Boc-amino-1,5-pentanediamine (162 mg). To a cooled (0° C.) mixture of the reactants in DMF (dry, 0.05 M) under nitrogen atmosphere were added EDCI.HCl (1.1 eq) and HOAt (0.1 eq). The mixture was stirred 1 hour at 0° C. and was allowed to reach room temperature and stirred until complete conversion (LCMS). The reaction mixture was poured into 10 eq (to DMF) of water and extracted with EtOAc (3×50 mL). The combined organic phases were successively washed with 0.5M KHSO$_4$ (50 mL), sat. aq. NaHCO$_3$ (50 mL) and brine (3×50 mL). The organic phase was dried over Na$_2$SO$_4$, filtered and concentrated in vacuo. INTERMEDIATE Ua (232 mg) was used in the next step without further purification.

Step B: According to general procedure B FINAL COMPOUND R-U (134 mg) was prepared. 1H NMR (400 MHz, CDCl$_3$): δ (ppm): 8.51 (1H, s), 7.22-6.45 (2H, broad s), 6.29-6.16 (1H, m), 3.64-3.41 (1H, m), 2.89-2.72 (1H, m), 2.69-2.40 (5H, m), 2.19 (3H, s), 2.18 (3H, s), 2.08 (3H, s), 1.83-1.68 (1H, m), 1.55 (3H, s), 1.45-1.33 (2H, m), 1.33-1.21 (1H, m), 1.20-1.03 (1H, m), 0.80-0.58 (2H, m).

1.2.14 Trolox™ 5-Aminopentylamide Hydrochloride (Compound U, S-Stereoisomer)

Step A: INTERMEDIATE Ub was prepared, using (S)-Trolox™ (200 mg) and 1-Boc-amino-1,5-pentanediamine (162 mg). To a cooled (0° C.) mixture of the reactants in DMF (dry, 0.05 M) under nitrogen atmosphere were added EDCI.HCl (1.1 eq) and HOAt (0.1 eq). The mixture was stirred 1 hour at 0° C. and was allowed to reach room temperature and stirred until complete conversion (LCMS). The reaction mixture was poured into 10 eq (to DMF) of water and extracted with EtOAc (3×50 mL). The combined organic phases were successively washed with 0.5M KHSO$_4$ (50 mL), sat. aq. NaHCO$_3$ (50 mL) and brine (3×50 mL). The organic phase was dried over Na$_2$SO$_4$, filtered and concentrated in vacuo. INTERMEDIATE Ub (242 mg) was used in the next step without further purification.

Step B: According to general procedure B FINAL COMPOUND S-U (164 mg) was prepared. 1H NMR (400 MHz, CDCl$_3$): δ (ppm): 8.51 (1H, broad s), 6.26-6.23 (2H, dd), 3.64-3.37 (1H, m), 2.91-2.74 (1H, m), 2.72-2.61 (3H, m), 2.60-2.42 (3H, m), 2.19 (3H, s), 2.18 (3H, s), 2.08 (3H, s), 1.83-1.67 (1H, m), 1.55 (3H, s), 1.47-1.34 (2H, m), 1.34-1.22 (1H, m), 1.21-1.05 (1H, m), 0.80-0.62 (2H, m).

1.2.15 Trolox™ 1-methylpiperidin-3-amide hydrochloride (Compound AF, S,R-Stereoisomer)

Step A: INTERMEDIATE AFa was prepared, using (R)-tert-butyl 3-aminopiperidine-1-carboxylate (200 mg). The substrate was dissolved in THF (dry, 0.1M) and cooled to 0° C. with an ice-bath. LiAlH$_4$ (5 eq 2.4 M in THF) was added dropwise to the cooled solution. The reaction mixture was stirred for 15 minutes at 0° C. and was allowed to reach room temperature. Then the mixture was refluxed until complete conversion (GCMS). The mixture was cooled to 0° C. and was sequentially quenched with water (0.2 mL), 15% NaOH solution (0.2 mL) and water (0.6 mL) and stirred for 1 hour. The precipitate was filtered off and 4M HCl in dioxane was added to the filtrate. The filtrate was concentrated in vacuo and triturated in MeCN/MeOH to obtain a white solid.

Step B: FINAL COMPOUND S,R-AF was prepared using (S)-Trolox™ (60 mg) and INTERMEDIATE AFa (45 mg). Both reactants were dissolved in DMF (dry, 0.25M). Triethylamine (2.5 eq) and PyBOP (1.2 eq) were added and the reaction mixture was stirred at room temperature until complete conversion (LCMS). The mixture was quenched with H$_2$O (20 ml). sat. aq. NaHCO$_3$ (30 ml) was added and the aqueous phase was extracted with EtOAc (3×30 ml). The combined organic phases were dried over Na$_2$SO$_4$, filtered and concentrated in vacuo. The crude material was purified by reversed phase column chromatography ((H$_2$O+0.01% (w/w) formic acid/MeCN) and freeze-dried to obtain FINAL COMPOUND S,R-AF (34 mg). $^1$H NMR (400 MHz, DMSO): δ (ppm): 8.19 (1H, s), 7.53 (1H, broad s), 7.14-7.12 (1H, d), 3.70 (1H, broad s), 2.59-2.36 (2H, m), 2.36-2.25 (1H, m), 2.24-2.11 (2H, m), 2.08 (3H, s), 2.07 (3H, s), 2.03 (3H, s), 1.99 (3H, s), 1.91-1.82 (1H, m), 1.81-1.68 (1H, m), 1.65-1.51 (1H, m), 1.50-1.40 (3H, m), 1.39-1.33 (3H, m).

1.2.16 Trolox™ piperidin-4-amide hydrochloride (Compound Z, Racemate)

Step A: INTERMEDIATE Za was prepared using Trolox™ (500 mg) and tert-butylaminopiperidine-1-carboxylate (400 mg). To a cooled (0° C.) mixture of the reactants in DMF (dry, 0.05 M) under nitrogen atmosphere were added EDCI.HCl (1.1 eq) and HOAt (0.1 eq). The mixture was stirred 1 hour at 0° C. and was allowed to reach room temperature and stirred until complete conversion (LCMS). The reaction mixture was poured into 10 eq (to DMF) of water. A white precipitate was formed and was filtered out. The residue was washed with water in the filter and dried. INTERMEDIATE Za (80 mg) was used in the next step without further purification.

Step B: According to general procedure B FINAL COMPOUND Z (60 mg) was prepared. 1H NMR (400 MHz, DMSO): δ (ppm): 8.32 (1H, s), 7.14-7.12 (1H, d), 3.78-3.63 (1H, m), 3.61-3.45 (1H, m), 3.13-3.02 (1H, m), 3.01-2.91 (1H, m), 2.83-2.65 (2H, m), 2.62-2.36 (2H, m), 2.24-2.13 (1H, m), 2.09 (3H, s), 2.07 (3H, s), 1.99 (3H, s), 1.86-1.68 (2H, m), 1.67-1.44 (2H, m), 1.43-1.24 (1H, m), 1.38 (3H, s).

1.2.17 Trolox™ prrolidin-3-amide hydrochloride (Compound AG, S,R-Stereoisomer)

Step A: According to general procedure A INTERMEDIATE AGa was prepared, using (S)-Trolox™ (100 mg) and (R)-tert-Butyl 3-aminopyrrolidine-1-carboxylate (74 mg). INTERMEDIATE AGa (110 mg) was used in the next step without further purification.

Step B: According to general procedure B FINAL COMPOUND S,R-AG (80 mg) was prepared. 1H NMR (400 MHz, DMSO): δ (ppm): 8.36 (1H, broad s), 7.60-7.59 (1H, d), 4.37-4.01 (2H, m), 3.15-2.98 (2H, m), 2.97-2.79 (1H, m), 2.77-2.59 (1H, m), 2.58-2.38 (2H, m), 2.26-2.10 (2H, m), 2.09 (3H, s), 2.07 (3H, s), 1.99 (3H, s), 1.85-1.54 (2H, m), 1.35 (3H, s).

1.2.18 Trolox™ pyrrolidin-3-amide hydrochloride (Compound AG, S,S-Stereoisomer)

Step A: According to general procedure A INTERMEDIATE AGb was prepared, using (S)-Trolox™ (100 mg) and (S)-tert-Butyl 3-aminopyrrolidine-1-carboxylate (74 mg). INTERMEDIATE AGb (115 mg) was used in the next step without further purification.

Step B: According to general procedure B FINAL COMPOUND S,S-AG (80 mg) was prepared. 1H NMR (400 MHz, DMSO): δ (ppm): 9.11 (2H, broad s), 7.74-7.72 (1H, d), 7.52 (1H, s), 4.48-4.20 (1H, s), 3.33-3.18 (2H, m), 3.17-3.09 (1H, m), 3.08-2.99 (1H, m), 2.62-2.38 (2H, m), 2.22-2.12 (1H, m), 2.10 (3H, s), 2.06 (3H, s), 1.99 (3H, s), 1.82-1.62 (2H, m), 1.37 (3H, s).

Example 2

Effect of Compounds on Protein Expression Levels of Fully Assembled Complex I and Complex II in Healthy and Patient Cells 2.1 Methods and Materials
2.1.1 Isolation of Mitochondria and OXPHOS Complexes To determine the effect of the compounds on the Complex I and II levels in normal and patient human skin fibroblasts, cells were treated with compound F(300 compound K (300 µM) or compound N (10 or 100 nM). The patient skin fibroblasts derive from patients with a mutation in different Complex I subunits and the control cells are human skin fibroblasts derived from healthy controls.

After 72 hours incubation with the compound, the (approx. $2 \times 10^6$) cells were harvested by trypsinization and washed twice with ice-cold phosphate-buffered saline (PBS; Life Technologies, Bleiswijk, Netherlands). Next, the cell suspensions were centrifuged for 5 min; 287×g; 4° C. and the cell pellets were snap-frozen in liquid nitrogen.

Prior to the isolation of the mitochondria and OXPHOS complexes, the pellets were thawed on ice and resuspended in 100 µl ice-cold PBS. For preparation of a mitochondria enriched fraction, 100 µl (4 mg/ml) digitonin (Sigma, Zwijndrecht, Netherlands) was added, and the cell suspension was left on ice for 10 min. Digitonin dissociates membranes that contain cholesterol. Therefore, it dissociates the cell membrane and the outer mitochondrial membrane, but not the inner mitochondrial membrane. Next, 1 ml ice-cold PBS was added to dilute the digitonin, followed by centrifugation (10 min; 15,600×g; 4° C.). After the centrifugation, the pellets contained a cell fraction which is enriched for mitoplasts. The supernatant was removed and the pellets were resuspended in 100 µl ice-cold PBS. Subsequently 1 ml ice-old PBS was added and the suspension was centrifuged (5 min; 15,600×g; 4° C.) again, followed by removal of the supernatant and resuspension of the pellet in 100 µl ice-cold PBS, addition of 1 ml ice-cold PBS and centrifugation (5 min; 15,600×g; 4° C.). The supernatant was removed with a syringe and needle and the pellets containing the mitoplast fraction were stored overnight (−20° C.).

The complexes of the OXPHOS system are extracted from the inner membrane with β-lauryl maltoside and aminocaproic acid. β-lauryl maltoside is a mild detergent which solubilizes the mitochondrial membrane and aminocaproic acid extracts the complexes. Aminocaproic acid is a zwitterionic salt that has a net charge of zero at pH 7 and, therefore, does not affect electrophoresis. Thus for isolation of the OXPHOS complexes, the pellets were thawed on ice and solubilized in 100 µl ACBT buffer containing 1.5 M ε-aminocaproic acid (Serva, Amsterdam, Netherlands) and 75 mM BisTris/HCl (pH 7.0) (Sigma). Subsequently 10 µl 20% (w/v) β-lauryl maltoside (Sigma) was added and the suspension was left on ice for 10 min. Next, the suspensions were centrifuged (30 min; 15,600×g; 4° C.) and the supernatants which contain the isolated complexes were transferred to a clean tube (L. G. Nijtmans, N. S. Henderson, I. J. Holt, Blue Native electrophoresis to study mitochondrial and other protein complexes, Methods 26 (2002) 327-334.).

2.1.2 Protein Assay

The protein concentration of the isolated OXPHOS complexes were determined using a Biorad Protein Assay (Biorad, Veenendaal, Netherlands). A standard curve with 0, 2, 4, 6, 8, 10 or 15 µl 1 mg/ml BSA (Sigma) was prepared in duplicate. To each sample of the standard curve 5 µl ACBT/LM was added, which consisted out of 150 µl ACBT as described under 2.1.1 and 15 µl 20% 0-lauryl maltoside. The Dye Reagent Concentrate 5× (Biorad) was 5× diluted with Milli Q and 2 ml of the diluted reagent was added to a sample of the standard curve or to 5 µl of the samples containing the isolated OXPHOS complexes. After an incubation period between 5 and 60 min, the extinction was measured at 595 nm.

2.1.3 BN-Page

Blue Native polyacrylamide gel electrophoresis (BN-PAGE) separates the five OXPHOS complexes from each other without dissociating them into their subunits. The separation is on basis of molecular mass. During the electrophoresis Serva Blue G (Serva) is used to give the protein complexes a charge for electrophoretic mobility, without dissociating the complexes. The electrophoresis is carried out in a gradient gel for a better separation of the complexes.

A native PAGE 4-16% Bis-Tris Gel (Life Technologies) was assembled in the XCell SureLock Mini-Cell (Life Technologies) according to the manufacturer's instructions. The slots were rinsed with Cathode buffer A, which consists of 50 mM Tricine (Sigma), 15 mM Bis-Tris pH 7.0 (Sigma) and 0.02% Serva Blue G (Serva). The slots were filled with cathode buffer B, which consists of 50 mM Tricine and 15 mM Bis-Tris pH 7.0. To each sample, blue native sample buffer was added in a 1:10 volume ratio. This sample buffer consists of 750 mM ε-aminocaproic acid, 50 mM Bis-Tris, 0.5 mM EDTA (Merck, Schiphol-Rijk, Netherlands), 5% Serva Blue G pH 7.0 and 20 µg protein of each sample was loaded onto the gel. The outer compartment was filled with 500 ml anode buffer (50 mM Bis-Tris pH 7.0) and the inner compartment was filled with cathode buffer A. The gel was ran 30 min 50V, 30 min 150V and subsequently the cathode buffer A was replaced by the cathode buffer B. The gel was ran again at 150V until the blue front had reached the bottom of the gel (L. G. Nijtmans, N. S. Henderson, I. J. Holt, Blue Native electrophoresis to study mitochondrial and other protein complexes, Methods 26 (2002) 327-334.).

2.1.4 Complex I or Complex II Protein Detection

To visualize the amount of complex I or complex II present in the BN-PAGE gels, the proteins were transferred to a PVDF membrane (Millipore, Amsterdam, Netherlands) using standard Western blotting techniques and detected by immunostaining. After the blotting and prior to blocking the PVDF membrane with 1:1 PBS-diluted Odyssey blocking buffer (Li-cor Biosciences, Cambridge, UK), the PVDF blot was stripped with stripping buffer for 15 min at 60° C. The stripping buffer consists of PBS, 0.1% Tween-20 (Sigma) and 2% SDS (Serva). For detection of the Complex I, a monoclonal primary antibody against NDUFA9 (39 kDa) (Molecular probes, Leiden, The Netherlands) was used at a final concentration of 1 µg/ml. To detect Complex II, a monoclonal antibody against the 70 kDa subunit of complex II was used (Molecular probes) at a final concentration of 0.5 µg/ml. Both primary antibodies were diluted in PBS, 0.1% Tween-20 and 2.5% Protifar Plus (Nutricia, Cuijk, The Netherlands) and allowed to bind to the complex for 4 hours at room temperature or overnight at 4° C. The bound primary antibodies were subsequently detected by IRDye 800 CW conjugated anti-Mouse antibody (Li-cor Biosciences) at a final concentration of 0.1 µg/ml. After drying the blot for 2 hrs in the dark, the IRDye was detected using a Odyssey Infrared Imaging System.

2.1.5 Statistical Analysis

Statistical analysis is performed using Origin Pro Plus software (version 6.1; OriginLab Corporation, Northampton, Mass., USA). Averages were compared using an unpaired independent Student's t-test with Bonferroni correction. Error bars indicate standard deviation (SD).

2.2 Results

Figure 1B:
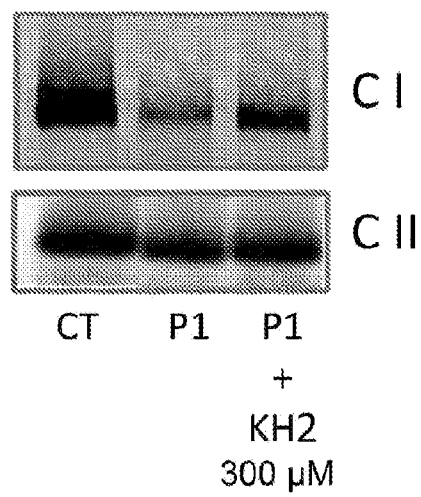
Figure 1C:
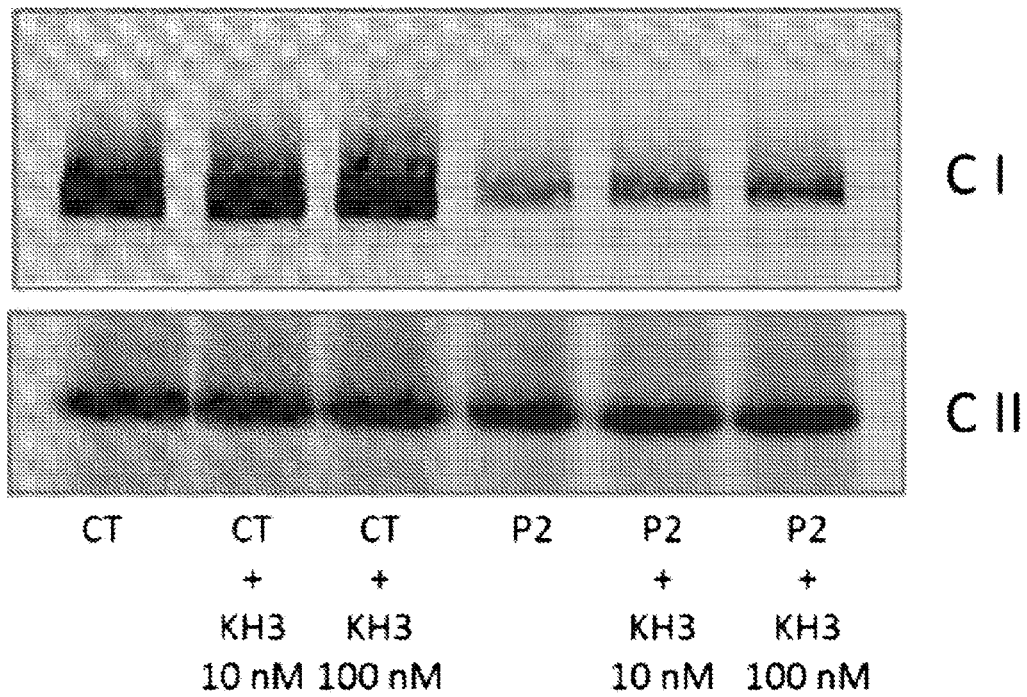
Figure 2A:
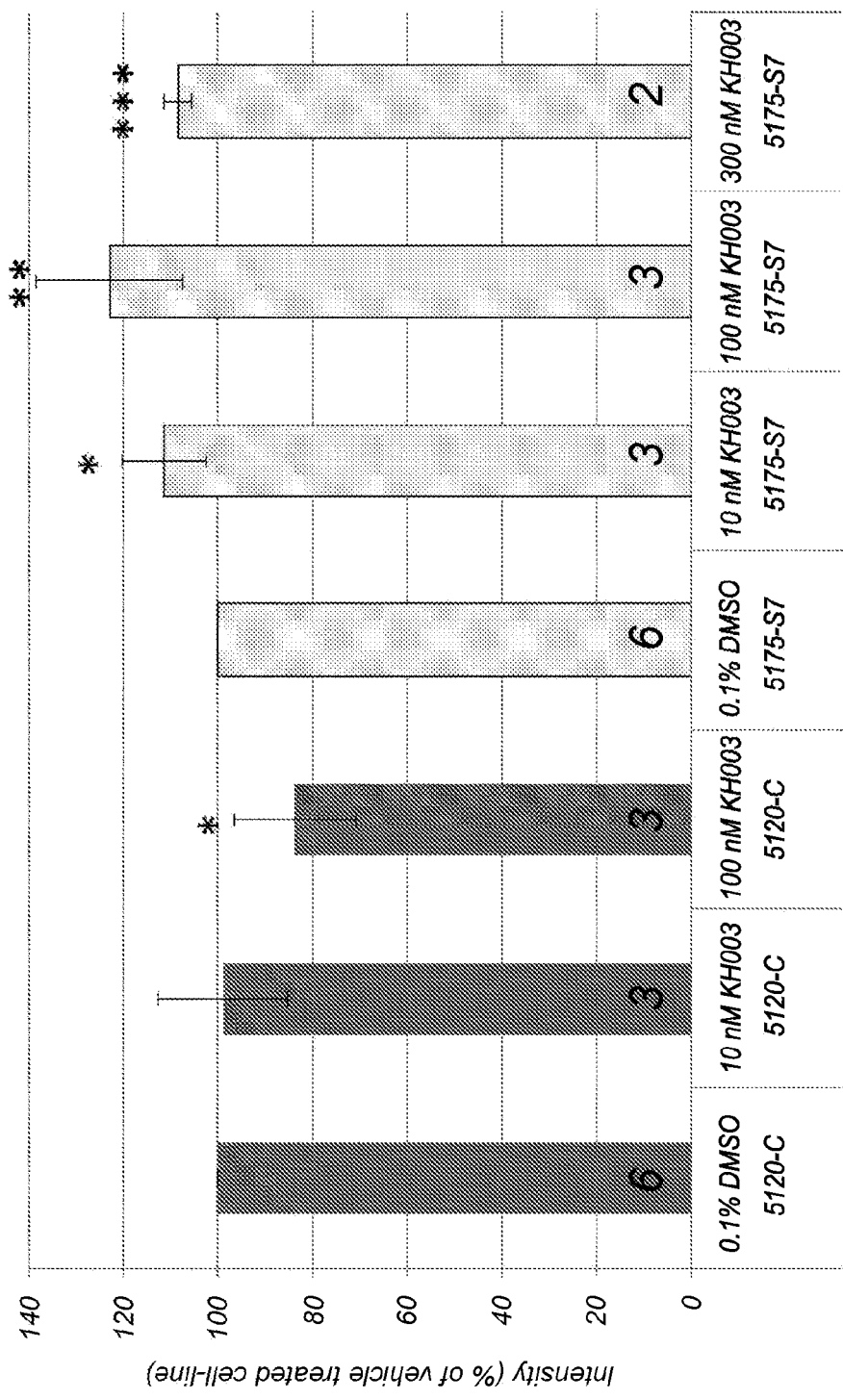
FIGS. 2a and 2b. The protein levels of fully assembled complex I (FIG. 2a) or complex II (FIG. 2b) were determined after exposure of the control cell line 5120-C or patient cell line 5175-S7 to compound N (KH003) at the indicated concentrations for 72 hours. The numerals in the bars indicate the number of independent experiments. *,  and * indicate significant differences ($P<0.05$, $P<0.01$ and $P<0.001$) relative to vehicle-treated control or patient cells.
Figure 2B:
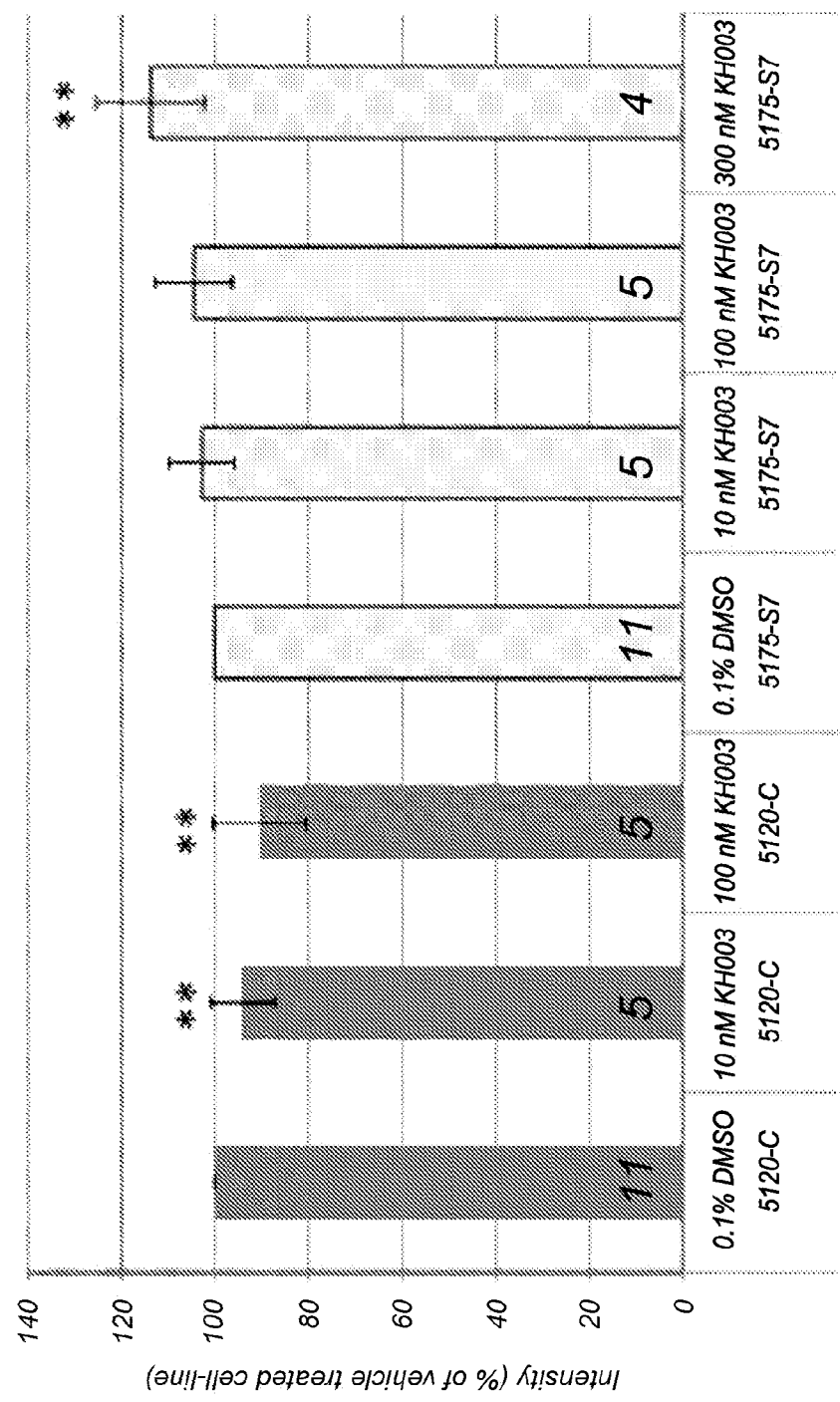

Addition of compound F to a patient-derived cell line containing a mutation in a complex I subunit results in an increase in fully assembled complex I protein levels (FIG. 1A). Also compound K increases the complex I protein levels in the same patient-derived cell line (FIG. 1B). Moreover, a dose-dependent increase in complex I protein levels is seen after the addition of 10 nM or 100 nM compound N to patient-derived cells (FIG. 1C). The increase in the above levels was quantified in FIG. 1 for complex I (panel A) and complex II (panel B). A statistically significant increase in complex I levels was observed after the addition of different concentrations of compound N to a patient-derived cell line. Also an increase in the level of fully assembled protein complex II was detected at the highest concentration of compound N. These data indicate that a mode of action of compounds F, K and N could involve increasing the amount of fully assembled complex I and potentially complex II protein levels.

Example 3

Effect of Compounds on the Increased Levels of CM-H$_2$DCF-Oxidizing Reactive Oxygen Species (ROS) in Patient Cells 3.1 Methods and Materials CM-H$_2$DCFDA is a cell-permeable reporter molecule for reactive oxygen species (ROS) that is converted into non-fluorescent and membrane-impermeable CM-H$_2$DCF following removal of its acetate groups by intracellular esterases. Upon oxidation by ROS, CM-H$_2$DCF is converted into fluorescent CM-DCF. It is widely accepted that a wide variety of ROS can be responsible for the CM-H$_2$DCF oxidation, making it a suitable reporter of cellular oxidant levels. The average cellular CM-DCF fluorescence intensity is considered an indirect measure of cellular ROS levels.

To measure the effect of the compounds on the intracellular ROS levels in different patient human skin fibroblasts, cells were seeded at a density of 1500 cells/well in a 96-well format and incubated with increasing concentrations of compounds F, K and N. Three days after treatment, the culture medium was replaced with 100 µl of CM-H$_2$DCFDA/well at a final concentration 1 (Life Technologies). The CM-H$_2$DCFDA solution is prepared by diluting a 1 mM stock solution (CM-H$_2$DCFDA dissolved in DMSO (Sigma)) 1:1000 into HT-buffer pH 7.4. This HT-buffer consists of 132 mM NaCl, 4 mM KCl, 1 mM MgCl$_2$, 10 mM HEPES, 1 mM CaCl$_2$ and 5 mM D-glucose).

The cell culture plate containing CM-H$_2$DCFDA was placed for exactly 10 minutes at 37° C. or room temperature. Next, the cells were washed twice with PBS and 100 µl 1× HT-buffer was added to each well containing cells in addition to 4 empty wells. In another 4 empty wells, 100 µl (5 µM) Fluorescein (Sigma) dissolved in HT-buffer was added. The wells without cells but with either HT-buffer or with HT-buffer and Fluorescein served to correct for respectively the background fluorescence or uneven illumination.

The CM-DCF fluorescence was measured with the BD Pathway 855 system, using the parameters: Exposure: 0.4; Gain: 10; Offset: 255. Using the BD pathway correction procedure all measurements were corrected for any background fluorescence and had a flat field correction to remove uneven illumination introduced by the BD pathway 855 system. Values were expressed as average CM-DCF intensity/cellular pixels/well and the values derived from the patient cell lines were calculated as percentage of the average value in control cell line C5120 treated with 0.1% DMSO only.

3.2.1 Results for Compounds F, K and N

Figure 3A:
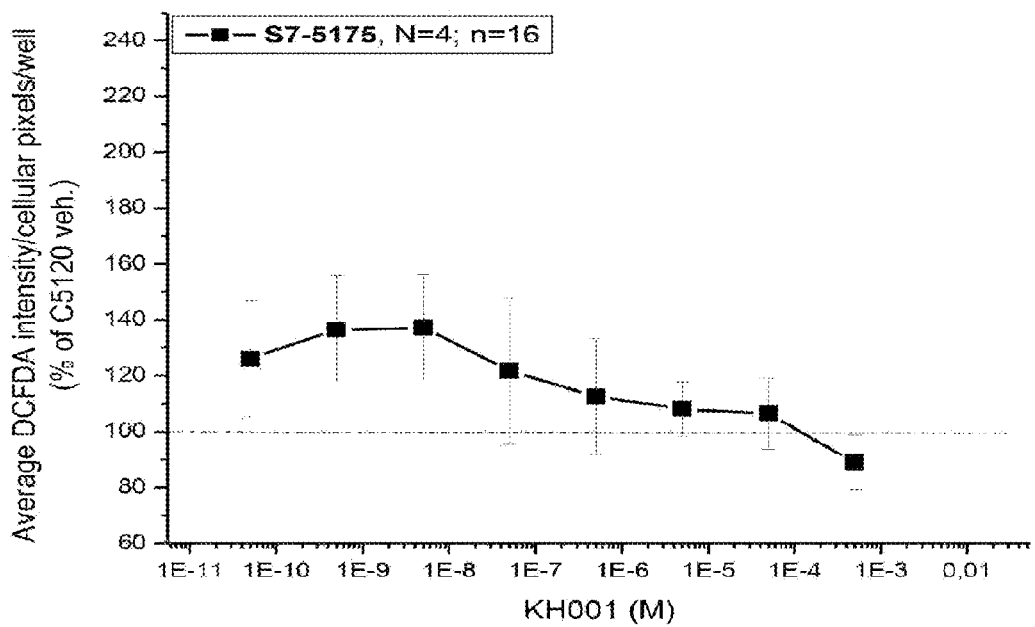
FIGS. 3a-3c. Patient cell lines as indicated in the figure, containing different mutations in the complex I subunit, were incubated with increasing concentrations of compound F (KH001.
Figure 3B:
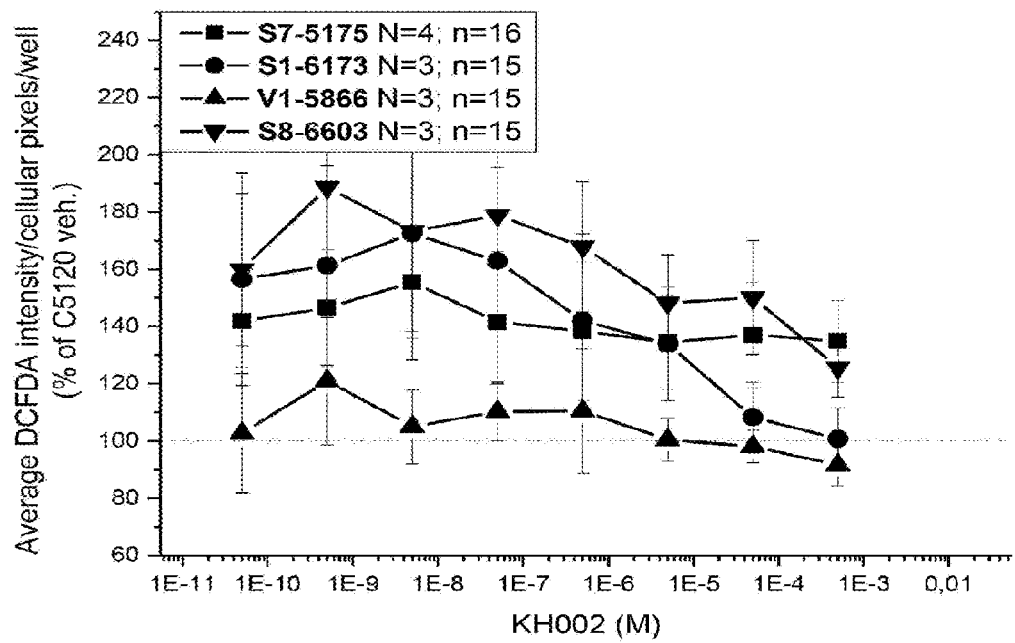
Figure 3C:
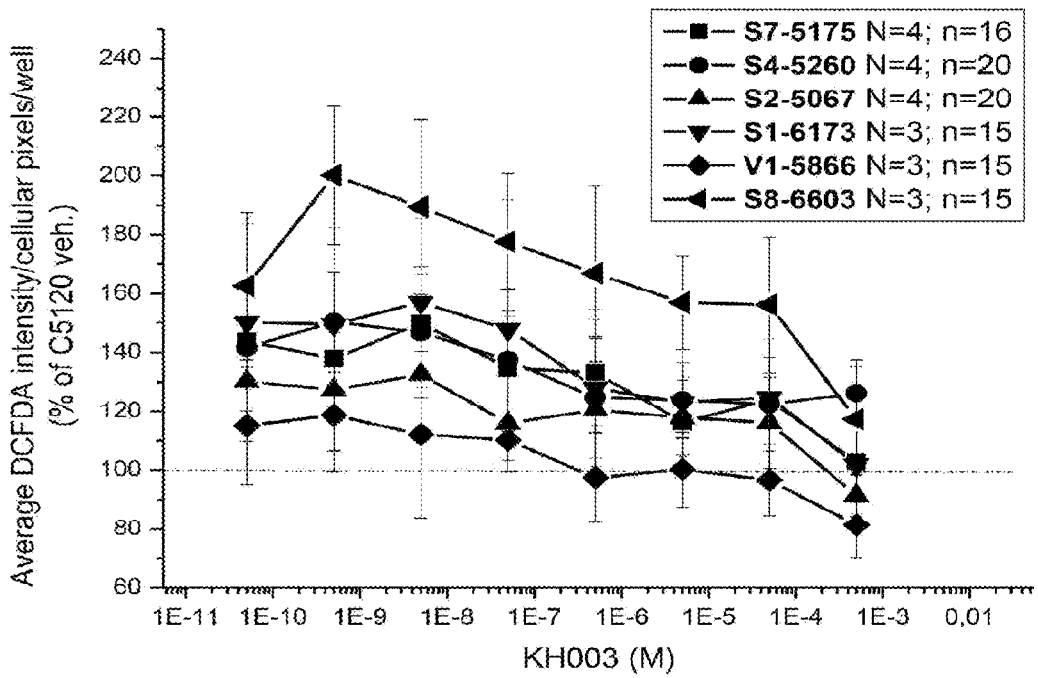

To determine whether the compounds had an effect on the intracellular ROS levels, one or several patient cell lines with increased ROS levels (W. J. H. Koopman, S. Verkaart, H. J. Visch, S. E. van Emst-de Vries, L. G. Nijtmans, J. A. Smeitink, P. H. Willems, Human NADH:ubiquinone oxidoreductase deficiency: radical changes in mitochondrial morphology?, Am J Physiol Cell Physiol 293 (2007) C22-C29) were exposed to increasing concentrations of the compounds F (FIG. 3A), K (FIG. 3B) or N (FIG. 3C). For all three compounds, there was a negative correlation observed between the compound concentration and the ROS levels, meaning that increased concentrations resulted in decreased ROS levels as determined by CM-DCF formation. As mitochondrial fragmentation might occur as a consequence of too high ROS levels (W. J. H. Koopman, S. Verkaart, H. J. Visch, S. E. van Emst-de Vries, L. G. Nijtmans, J. A. Smeitink, P. H. Willems, Human NADH:ubiquinone oxidoreductase deficiency: radical changes in mitochondrial morphology?, Am J Physiol Cell Physiol 293 (2007) C22-C29; Distelmaier F., Valsecchi, F., Forkink, M., van Emst-de Vries, S., Swarts, H., Rodenburg, R., Verwiel, E., Smeitink, J., Willems, P. H. G. M., Koopman, W. J. H. (2012) Trolox™-sensitive ROS regulate mitochondrial morphology, oxidative phosphorylation and cytosolic calcium handling in healthy cells. Antioxidants and redox signaling. (in press), PMID 22559215) the compounds could at least partly exert their therapeutic effect through decreasing ROS levels back to physiological levels.

3.2.2 Results for Additional Compounds

Further compounds capable of reducing intracellular ROS levels are listed in Table 2. The compounds were tested for their effect on decreasing the intracellular ROS levels in a patient cell line (S7-5175 cells, which are fibroblasts from a patient with a mutation in the NDUFS7 gene) with increased ROS levels, in a DCFDA assay, essentially as described above in 3.1. A dose-response curve was determined for each compound listed, from which the EC$_{50}$ (potency), i.e. the concentration of the compound that gives half-maximal response, was calculated and indicated in Table 2.

TABLE 2

Potencies of compounds in the DCFDA assay.

| Code | Compound | EC$_{50}$ in DCFDA assay* |
|---|---|---|
| KH001 | rac-F | + |
| KH003 | R,S-N/S,S-N (1/1) | ++ |
| KH004 | R,S-O/S,S-O (1/1) | + |
| KH137 | rac-Z | ++ |
| KH167 | R-T | + |
| KH168 | S-T | + |
| KH174 | R,R-X | ++ |
| KH175 | R,S-X | ++ |
| KH176 | S,R-X | +++ |
| KH177 | S,S-X | ++ |
| KH185 | R-U | ++ |
| KH186 | S-U | ++ |
| KH189 | R-V | +++ |
| KH190 | S-V | + |
| KH193 | R,trans-AE | ++ |
| KH194 | S,trans-AE | ++ |
| KH204 | S,R-AF | +++ |
| KH213 | S-AH | ++ |
| KH217 | S,R-AG | ++ |
| KH218 | S,S-AG | ++ |

*+ indicates an EC$_{50}$ in the range of 10-100 µM;
++ indicates an EC$_{50}$ in the range of 1-10 µM; and,
+++ indicates an EC$_{50}$ in the range of 0.1-1 µM.

Example 4

Effect of Compound I and J on Protein Expression Levels of Fully Assembled Complex I Compounds I and J produce a slight reduction in the expression of complex I in healthy control cell lines, whereas the compounds produce a dramatic reduction in the expression of complex I in patient cell lines, whereby the effect of compound J is stronger than the effect of compound I.

Example 5

In Vivo Effect of Compound N on Grip Strength in Ndufs4 Knockout Mice

Animals and Treatments:

Ndufs4 knockout (KO) and wild-type (WT) mice were generated by crossing Ndufs4 heterozygote males and females (Kruse S E, et al., 2008, Cell Metab 7:312-320). The total number (n) of animals used in this project is as follows: Vehicle WT: 7, compound N (KH003) WT: 7, Vehicle KO: 5, compound N KO: 5. Animals were tested at 3, 5 and 6 weeks of age. Animals received either vehicle (control) injections, consisting of sterile water, or compound N at a dose of 400 mg/kg, with a dose volume of 4 ml/kg. Animals were injected twice a day (2 ml/kg per injection). Injections began during week 3 of life, and continued daily until the conclusion of the experiment in week 6.

Data Analysis:

All data are expressed as mean±SEM. Data were analyzed using a one-way ANOVA in SPSS version 20.0. Significant overall effects (i.e. genotype, treatment and/or genotype*treatment interaction) were further analyzed using Fisher's PLSD post-hoc analyses.

Grip Strength Paradigm:

The grip strength test is designed to measure muscular strength in rodents. The apparatus consists of a single bar, which the animal will grasp by instinct. Once the bar has been grasped, the experimenter gently retracts the animal until the animal is forced to release the bar. The amount of force exerted by the animal on the bar is measured in Pond (p) (1 p=1 gram). The grip strength test is repeated 5 times and the average force exerted is used as the quantitative readout. All measurements were corrected for body weight, using the following equation:

Grip Strength Score=((week $X$ trials 1+2+3+4+5)/5)/ Average Body Weight week $X$ (g) (Week $X$=week 3, 5 or 6)

Testing Procedure:

On testing days, animals received their morning injection 30 minutes prior to their testing time. After injections, the animals were placed in the testing room for a 30 minute acclimation period.

Figure 4:
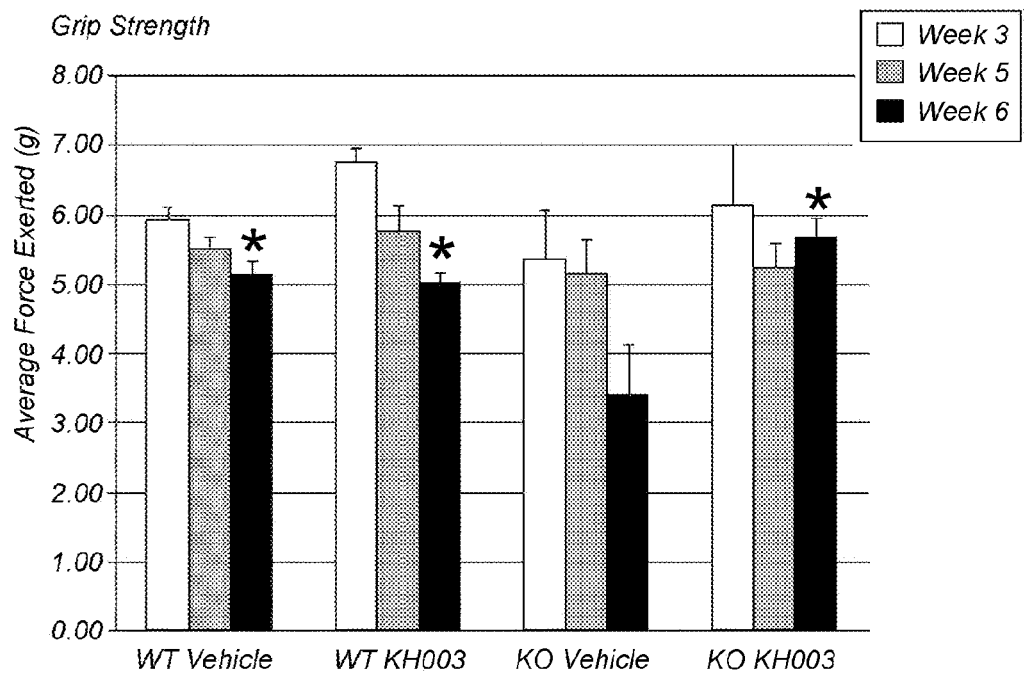
FIG. 4. In vivo effect of compound N (KH003) on Grip Strength in Ndufs4 knockout mice, tested as described in Example 4. KO=Ndufs4 knockout mice; WT=corresponding wild type mice; Vehicle=control injections without active ingredient; KH003=injections with compound N as active ingredient.

Results:

Chronic treatment with compound N resulted in significantly improved grip strength in the KO animals at week 6 of testing, compared to vehicle knockouts (p<0.002) as shown in FIG. 4. Also, KO animals treated with compound N were no longer significantly different compared to wild type animals in both treatment groups at week 6, indicating that compound N treatment significantly improved muscle strength performance, rendering it comparable to wild types, at this time point. There were no significant differences between groups in weeks 3 and 5.

Similar results as obtained with compound N were obtained with compound S,R-X (KH176), when administered at a 10 times lower dosage compared to compound N, i.e. a dose of 40 mg/kg, with a dose volume of 4 ml/kg (2 ml/kg injections twice a day) (data not shown).

The invention claimed is:

1. A compound of general formula (I):

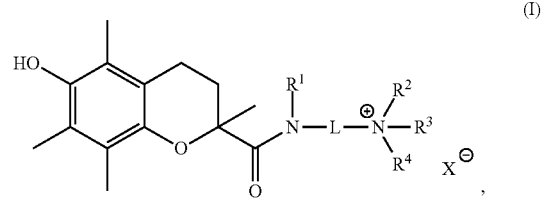

(I)

wherein

L is a linker comprising 1 to 10 optionally substituted backbone atoms selected from carbon, nitrogen and oxygen; and $R^1$ and $R^2$ are each independently selected from hydrogen and $C_1$-$C_6$ alkyl, or $R^1$ and $R^2$ are joined together to form a second linker between the amide nitrogen atom and the cationic nitrogen atom, or $R^1$ is joined with a backbone atom of the linker L in a cyclic structure and/or $R^2$ is joined with a backbone atom of the linker L in a cyclic structure; and $R^3$ is selected from hydrogen and $C_1$-$C_6$ alkyl, wherein the alkyl moiety may be substituted with one or more halogen atoms or (halo)alkoxy moieties, or $R^3$ is absent when the cationic nitrogen atom is part of an imine moiety; and $R^4$ is selected from hydrogen and $C_1$-$C_6$ alkyl, wherein the alkyl moiety may be substituted with one or more halogen atoms or (halo)alkoxy moieties; and X— is a pharmaceutically acceptable anion, wherein the compound is not:

(i) the compound of formula (I), wherein L= —(CH$_2$)$_3$—, $R^1$=H, $R^2$=H, $R^3$=H, $R^4$=H and X=Cl;

(ii) the compound of formula (I), wherein L= —(CH$_2$)$_2$—CHR$^{1'}$—CH$_2$—NH—(CH$_2$)$_4$—, $R^1$=R$^{1'}$=—(CH$_2$)$_2$—, $R^2$=H, $R^3$=—(CH$_2$)$_2$—CH$_3$, $R^4$=H and X=Cl;

(iii) the compound of formula (I), wherein L= —(CH$_2$)$_3$—, $R^1$=H, $R^2$=H, $R^3$=H, $R^4$=H; X=TFA, which is in the S-configuration at the 2-position;

(iv) 1-[2-(6-amino-4-methyl-2-pyridinyl)ethyl]-4-[(3,4-dihydro-6-hydroxy-2,5,7,8-tetramethyl-2H-[1]-benzopyran-2-yl)carbonyl]-piperazine hydrochloride;

(v) 1-[4-(2-amino-6-pyridinyl)-3-butynyl]-4-[(3,4-dihydro-6-hydroxy-2,5,7,8-tetramethyl-2H-[1]-benzopyran-2-yl)carbonyl]-piperazine hydrochloride; or (vi) N-[4-(6-amino-4-methyl-2-pyridinyl)butyl]-6-hydroxy-2,5,7,8-tetramethyl-2-chromanecarboxamide fumarate.

2. The compound according to claim 1, wherein the backbone atoms of L are represented by $C_{n-m}N_m$, wherein n designates the total number of atoms in the backbone, and m the number of nitrogen atoms in the backbone, wherein n=2–7 and m=0–3.

3. The compound according to claim 1, wherein X=Cl, I, TFA or formate.

4. The compound according to claim 1, wherein
L=—(CH$_2$)$_2$—, R$^1$—R$^2$=—(CH$_2$)$_2$—, R$^3$=H, R$^4$=H, X=Cl; or
L=—(CH$_2$)$_2$—, R$^1$=H, R$^2$=H, R$^3$=H, R$^4$=H; X=Cl; or
L=—(CH$_2$)$_2$NHC(O)CH$_2$—, R$^1$=H, R$^2$=H, R$^3$=H, R$^4$=H; X=Cl; or
L=—(CH$_2$)$_2$NHC(NH$_2$)=, R$^1$=H, R$^2$=H, R$^3$=absent, R$^4$=H; X=TFA; or
L=—(CH$_2$)$_2$NHC(O)CH$_2$NHC(NH$_2$)=, R$^1$=H, R$^2$=H, R$^3$=absent, R$^4$=H; X=TFA; or
L=—(CH$_2$)$_3$NHC(NH$_2$)=, R$^1$=H, R$^2$=H, R$^3$=absent, R$^4$=H; X=TFA; or
L=—(CH$_2$)$_3$—, R$^1$=H, R$^2$=Me, R$^3$=Me, R$^4$=Me; X=I; or
L=—(CH$_2$)$_2$—, R$^1$=H, R$^2$=Me, R$^3$=Me, R$^4$=Me; X=I; or
L=—(CH$_2$)$_2$NHC(Me)=, R$^1$=H, R$^2$=H, R$^3$=absent, R$^4$=H; X=Cl; or
L=—(CH$_2$)$_2$NHC(O)CH$_2$NHC(Me)=, R$^1$=H, R$^2$=H, R$^3$=absent, R$^4$=H; X=Cl; or
L=—(CH$_2$)$_3$NHC(Me)=, R$^1$=H, R$^2$=H, R$^3$=absent, R$^4$=H; X=Cl; or
L=—(CH$_2$)$_2$NR$^{1'}$C(NH$_2$)=, R$^1$—R$^{1'}$=—(CH$_2$)$_2$—, R$^2$=H, R$^3$=absent, R$^4$=H; X=TFA; or
L=—C(CO$_2$H)(CH$_2$)$_3$—, R$^1$=H, R$^2$=H, R$^3$=H, R$^4$=H; X=Cl; or
L=—C(CO$_2$H)(CH$_2$)$_3$NHC(NH$_2$)=, R$^1$=H, R$^2$=H, R$^3$=absent, R$^4$=H; X=Cl; or
L=—C(CO$_2$H)CH$_2$—, R$^1$=H, R$^2$=H, R$^3$=H, R$^4$=H; X=Cl; or
L=—C(CO$_2$H)(CH$_2$)$_2$—, R$^1$=H, R$^2$=H, R$^3$=H, R$^4$=H; X=Cl; or
L=—C(CO$_2$H)(CH$_2$)$_3$—, R$^1$=H, R$^2$=H, R$^3$=H, R$^4$=H; X=Cl; or
L=—C(CO$_2$H)(CH$_2$)$_3$—, R$^1$=H, R$^2$=Me, R$^3$=Me, R$^4$=H; X=Cl; or
L=—(CH$_2$)$_4$—, R$^1$=H, R$^2$=H, R$^3$=H, R$^4$=H; X=Cl; or
L=—(CH$_2$)$_5$—, R$^1$=H, R$^2$=H, R$^3$=H, R$^4$=H; X=Cl; or
L=—(CH$_2$)$_4$—, R$^1$=H, R$^2$=Me, R$^3$=Me, R$^4$=H; X=Cl; or
L=—CHR$^{2'}$C(O)—, R$^1$=H, R$^2$—R$^{2'}$=—(CH$_2$)$_3$—, R$^3$=H, R$^4$=H; X=Cl; or
L=—CHR$^{2'}$CH$^2$—, R$^1$=H, R$^2$—R$^{2'}$=—(CH$_2$)$_3$—, R$^3$=H, R$^4$=H; X=Cl; or
L=—CHR$^5$CH$_2$NR$^{5'}$C(Me)=, R$^1$=H, R$^2$=H, R$^5$—R$^{5'}$=—(CH$_2$)$_3$—, R$^3$=absent, R$^4$=H; X=Cl; or
L=—CHR$^{2'}$(CH$_2$)$_2$—, R$^1$=H, R$^2$—R$^{2'}$=—(CH$_2$)$_2$—, R$^3$=H, R$^4$=H; X=Cl; or
L=—(CH$_2$)$_2$CHR$^{1'}$—, R$^1$—R$^{1'}$=—(CH$_2$)$_2$—, R$^2$=H, R$^3$=H, R$^4$=H; X=Cl; or
L=—(CH$_2$)$_2$CHR$^{1'}$NHC(O)C(Me)-, R$^1$—R$^{1'}$=—(CH$_2$)$_2$—, R$^2$=H, R$^3$=H, R$^4$=H; X=Cl; or
L=—CH$_2$CHR$^{1'}$—, R$^1$—R$^{1'}$=—(CH$_2$)$_3$—, R$^2$=H, R$^3$=H, R$^4$=H; X=Cl; or
L=—CH$_2$CHR$^{1'}$NHC(Me)=, R$^1$—R$^{1'}$=—(CH$_2$)$_3$—, R$^2$=H, R$^3$=absent, R$^4$=H; X=Cl; or
L=—CHR$^5$(CH$_2$)$_2$CHR$^{5'}$—, R$^1$=H, R$^2$=H, R$^5$R$^{5'}$=—(CH$_2$)$_2$—, R$^3$=H, R$^4$=H; X=Cl; or
L=—CHR$^{2'}$CH$_2$—, R$^1$—R$^{1'}$=H, R$^2$—R$^{2'}$=—(CH$_2$)$_3$—, R$^3$=Me, R$^4$=H; X=Cl; or
L=—CHR$^{2'}$CH$_2$—, R$^1$=H, R$^2$—R$^{2'}$=—(CH$_2$)$_2$—, R$^3$=H, R$^4$=H; X=Cl; or
L=—CHR$^{2'}$(CH$_2$)$_2$—, R$^1$=H, R$^2$—R$^{2'}$=—(CH$_2$)$_2$—, R$^3$=Me, R$^4$=H; X=Cl.

5. The compound according to claim 4, wherein
L=—(CH$_2$)$_2$NHC(O)CH$_2$NHC(NH$_2$)=, R$^1$=H, R$^2$=H, R$^3$=absent, R$^4$=H; X=TFA; or
L=—(CH$_2$)$_2$NHC(O)CH$_2$NHC(Me)=, R$^1$=H, R$^2$=H, R$^3$=absent, R$^4$=H; X=Cl; or
L=—C(CO$_2$H)(CH$_2$)$_3$—, R$^1$=H, R$^2$=H, R$^3$=H, R$^4$=H; X=Cl; or
L=—C(CO$_2$H)(CH$_2$)$_3$NHC(NH$_2$)=, R$^1$=H, R$^2$=H, R$^3$=absent, R$^4$=H; X=Cl; or
L=—(CH$_2$)$_5$—, R$^1$=H, R$^2$=H, R$^3$=H, R$^4$=H; X=Cl; or
L=—(CH$_2$)$_4$—, R$^1$=H, R$^2$=Me, R$^3$=Me, R$^4$=H; X=Cl; or
L=—CHR$^{2'}$CH$_2$—, R$^1$=H, R$^2$—R$^{2'}$=—(CH$^2$)$^3$—, R$^3$=H, R$^4$=H; X=Cl; or
L=—CHR$^{2'}$(CH$_2$)$_2$—, R$^1$=H, R$^2$—R$^{2'}$=—(CH$_2$)$_2$—, R$^3$=H, R$^4$=H; X=Cl; or
L=—CHR$^5$(CH$_2$)$_2$CHR$^{5'}$, R$^1$=H, R$^2$=H, R$^5$—R$^{5'}$=—(CH$_2$)$_2$—, R$^3$=H, R$^4$=H; X=Cl; or
L=—CHR$^{2'}$CH$_2$—, R$^1$=H, R$^2$—R$^{2'}$=—(CH$_2$)$_3$—, R$^3$=Me, R$^4$=H; X=Cl; or
L=—CHR$^{2'}$(CH$_2$)$_2$—, R$^1$=H, R$^2$—R$^{2'}$=—(CH$_2$)$_2$—, R$^3$=Me, R$^4$=H; X=Cl.

6. The compound according to claim 4, wherein
L=—(CH$_2$)$_3$—, R$^1$=H, R$^2$=Me, R$^3$=Me, R$^4$=Me; X=I; or
L=—(CH$_2$)$_2$—, R$^1$=H, R$^2$=Me, R$^3$=Me, R$^4$=Me; X=I.

7. A pharmaceutical or cosmetic composition comprising a compound according to claim 1 and a physiologically acceptable carrier.

8. A method of modulating at least one of mitochondrial morphology and expressing OXPHOS enzymes, comprising contacting the mitochondria with a compound according to claim 1.

9. A method of treating or suppressing symptoms associated with a mitochondrial disorder or condition associated with mitochondrial dysfunction, comprising administering to a subject in need thereof a compound of general formula (I):

(I)

wherein
L is a linker comprising 1 to 10 optionally substituted backbone atoms selected from carbon, nitrogen and oxygen; and R$^1$ and R$^2$ are each independently selected from hydrogen and C$_1$-C$_6$ alkyl, or R$^1$ and R$^2$ are joined together to form a second linker between the amide nitrogen atom and the cationic nitrogen atom, or R$^1$ is joined with a backbone atom of the linker L in a cyclic structure and/or R$^2$ is joined with a backbone atom of the linker L in a cyclic structure; and R$^3$ is selected from hydrogen and C$_1$-C$_6$ alkyl, wherein the alkyl moiety may be substituted with one or more halogen atoms or (halo)alkoxy moieties, or R$^3$ is absent when the cationic nitrogen atom is part of an imine moiety; and R⁴ is selected from hydrogen and C₁-C₆ alkyl, wherein the alkyl moiety may be substituted with one or more halogen atoms or (halo)alkoxy moieties; and X⁻ is a pharmaceutically acceptable anion.

10. The method according to claim 9, wherein
L=—(CH₂)₂NHC(O)CH₂NHC(NH₂)=, R¹=H, R²=H, R³=absent, R⁴=H; X=TFA; or
L=—(CH₂)₂NHC(O)CH₂NHC(Me)=, R¹=H, R²=H, R³=absent, R⁴=H; X=Cl; or
L=—C(CO₂H)(CH₂)₃—, R¹=H, R²=H, R³=H, R⁴=H; X=Cl; or
L=—C(CO₂H)(CH₂)₃NHC(NH₂)=, R¹=H, R²=H, R³=absent, R⁴=H; X=Cl; or
L=—(CH₂)₅—, R¹=H, R²=H, R³=H, R⁴=H; X=Cl; or
L=—(CH₂)₄—, R¹=H, R²=Me, R³=Me, R⁴=H; X=Cl; or
L=—CHR²'CH₂—, R¹=H, R²—R²'=—(CH₂)₃—, R³=H, R⁴=H; X=Cl; or
L=—CHR²'(CH₂)₂—, R¹=H, R²—R²'=—(CH₂)₂—, R³=H, R⁴=H; X=Cl; or
L=—CHR⁵(CH₂)₂CHR⁵', R¹=H, R²=H, R⁵—R⁵'=—(CH₂)₂—, R³=H, R⁴=H; X=Cl; or
L=—CHR²'CH₂—, R¹=H, R²—R²'=—(CH₂)₃—, R³=Me, R⁴=H; X=Cl; or
L=—CHR²'(CH₂)₂—, R¹=H, R²—R²'=—(CH₂)₂—, R³=Me, R⁴=H; X=Cl.

11. The method according to claim 9, wherein the mitochondrial disorder is selected from the group consisting of: Myoclonic epilepsy; Myoclonic Epilepsy with Ragged Red Fibers (MERRF); Leber's Hereditary Optic Neuropathy (LHON); neuropathy ataxia and retinitis pigmentosa (NARP); Mitochondrial Myopathy, Encephalopathy, Lactacidosis, Stroke (MELAS); Leigh syndrome; Leigh-like syndrome; Dominant Optic atrophy (DOA); Kearns-Sayre Syndrome (KSS); Maternally Inherited Diabetes and Deafness (MIDD); Alpers-Huttenlocher syndrome; Ataxia Neuropathy spectrum; Chronic Progressive External Ophthalmoplegia (CPEO); Pearson syndrome; Mitochondrial Neuro-Gastro-Intestinal Encephalopathy (MNGIE); Sengers syndrome; 3-methylglutaconic aciduria, sensorineural deafness, encephalopathy and neuro-radiological findings of Leigh-like syndrome (MEGDEL); myopathy; mitochondrial myopathy; cardiomyopathy; and encephalomyopathy, SURF1 (COX deficient Leigh syndrome due to complex IV surfeit protein deficiency) and isolated or combined OXPHOS deficiencies with so far unsolved genetic defect including disturbed pyruvate oxidation and ATP plus PCr production rates.

12. The method according to claim 9, wherein the condition associated with mitochondrial dysfunction is selected from the group consisting of: Friedreich's Ataxia (FRDA); renal tubular acidosis; Parkinson's disease; Alzheimer's disease; amyotrophic lateral sclerosis (ALS); Huntington's disease; developmental pervasive disorders; hearing loss; deafness; diabetes; ageing; and adverse drug effects hampering mitochondrial function.

13. The method according to claim 9, further comprising assessing the efficacy of the therapy using a measurable clinical marker.

14. The method according to claim 11, wherein the clinical marker is one or more markers selected from the group consisting of lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; aminoacids, in particular alanine, citrulline and proline in whole blood, plasma or cerebrospinal fluid, organic acids in bodyfluids; FGF21 in serum and skeletal muscle; phosphocreatine levels, NADH (NADH+H⁺) or NADPH (NADPH+H⁺) levels; NAD or NADP levels; ATP levels; anaerobic threshold; reduced coenzyme Q (CoQ^red) levels; oxidized coenzyme Q (CoQ^os) levels; total coenzyme Q (CoQ^tot) levels; oxidized cytochrome C levels; reduced cytochrome C levels; oxidized cytochrome C/reduced cytochrome C ratio; acetoacetate levels, beta-hydroxy butyrate levels, acetoacetate/betahydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2).

15. A cosmetic method for delaying further aging of the skin in a subject, comprising administering to the skin of the subject an effective amount of a composition comprising a compound of general formula (I):

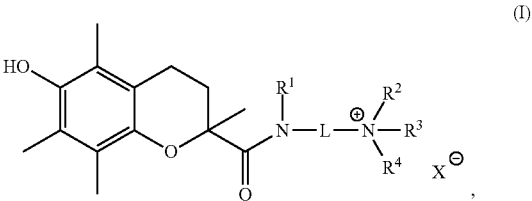

(I)

wherein
L is a linker comprising 1 to 10 optionally substituted backbone atoms selected from carbon, nitrogen and oxygen; and R¹ and R² are each independently selected from hydrogen and C₁-C₆ alkyl, or R¹ and R² are joined together to form a second linker between the amide nitrogen atom and the cationic nitrogen atom, or R¹ is joined with a backbone atom of the linker L in a cyclic structure and/or R² is joined with a backbone atom of the linker L in a cyclic structure; and R³ is selected from hydrogen and C₁-C₆ alkyl, wherein the alkyl moiety may be substituted with one or more halogen atoms or (halo)alkoxy moieties, or R³ is absent when the cationic nitrogen atom is part of an imine moiety; and R⁴ is selected from hydrogen and C₁-C₆ alkyl, wherein the alkyl moiety may be substituted with one or more halogen atoms or (halo)alkoxy moieties; and X⁻ is a pharmaceutically acceptable anion.

16. The method according to claim 15, wherein
L=—(CH₂)₂NHC(O)CH₂NHC(NH₂)=, R¹=H, R²=H, R³=absent, R⁴=H; X=TFA; or
L=—(CH₂)₂NHC(O)CH₂NHC(Me)=, R¹=H, R²=H, R³=absent, R⁴=H; X=Cl; or
L=—C(CO₂H)(CH₂)₃—, R¹=H, R²=H, R³=H, R⁴=H; X=Cl; or
L=—C(CO₂H)(CH₂)₃NHC(NH₂)=, R¹=H, R²=H, R³=absent, R⁴=H; X=Cl; or
L=—(CH₂)₅—, R¹=H, R²=H, R³=H, R⁴=H; X=Cl; or
L=—(CH₂)₄—, R¹=H, R²=Me, R³=Me, R⁴=H; X=Cl; or
L=—CHR²'CH₂—, R¹=H, R²—R²'=—(CH₂)₃—, R³=H, R⁴=H; X=Cl; or L=—CHR²'(CH₂)₂—, R¹=H, R²—R²'=—(CH₂)₂—, R³=H, R⁴=H; X=Cl; or L=—CHR⁵(CH₂)₂CHR⁵'—, R¹=H, R²=H, R⁵—R⁵'=—(CH₂)₂—, R³=H, R⁴=H; X=Cl; or L=—CHR²'CH₂—, R¹=H, R²—R²'=—(CH₂)₃—, R³=Me, R⁴=H; X=Cl; or L=—CHR²'(CH₂)₂—, R¹=H, R²—R²'=—(CH₂)₂—, R³=Me, R⁴=H; X=Cl.

17. The method according to claim 9, wherein the subject is at risk of developing clinical symptoms of mitochondrial disorder or condition associated with mitochondrial dysfunction.

* * * * *